(12) United States Patent
Maroschek

(10) Patent No.: US 11,026,780 B2
(45) Date of Patent: Jun. 8, 2021

(54) CARTRIDGE FOR AN INJECTOR FOR IMPLANTING AN INTRAOCULAR LENS

(71) Applicant: IOLUTION GmbH, Hamburg (DE)

(72) Inventor: Christoph Maroschek, Hamburg (DE)

(73) Assignee: IOLUTION GMBH, Hamburg (DE)

( * ) Notice: Subject to any disclaimer, the term of this patent is extended or adjusted under 35 U.S.C. 154(b) by 126 days.

(21) Appl. No.: 16/315,783

(22) PCT Filed: Jul. 5, 2017

(86) PCT No.: PCT/DE2017/000193
§ 371 (c)(1),
(2) Date: Jan. 7, 2019

(87) PCT Pub. No.: WO2018/006889
PCT Pub. Date: Jan. 11, 2018

(65) Prior Publication Data
US 2019/0254812 A1    Aug. 22, 2019

(30) Foreign Application Priority Data
Jul. 7, 2016  (DE) .................... 10 2016 008 195.3

(51) Int. Cl.
*A61F 2/16*    (2006.01)
(52) U.S. Cl.
CPC ............ *A61F 2/1678* (2013.01); *A61F 2/167* (2013.01)

(58) Field of Classification Search
CPC .......... A61F 2/1662–1678; A61F 9/007; A61F 2002/1681; A61F 2/148
See application file for complete search history.

(56) References Cited

U.S. PATENT DOCUMENTS

| 2008/0058830 A1 | 3/2008 | Cole et al. |
| 2014/0066946 A1 | 3/2014 | Aguilera et al. |
| 2014/0135784 A1* | 5/2014 | Maroscheck ......... A61F 2/1678 606/107 |

FOREIGN PATENT DOCUMENTS

| EP | 2 926 770 A1 | 10/2015 |
| WO | 00/45746 A1 | 8/2000 |
| WO | 2012/155887 A1 | 11/2012 |

* cited by examiner

*Primary Examiner* — Katherine M Shi
(74) *Attorney, Agent, or Firm* — BakerHostetler

(57) ABSTRACT

The present invention relates to a cartridge for an injector system, including a folding body for implanting an intraocular lens into an eye. The cartridge comprises a receiving region for at least one lens and at least one movable haptic slider for sliding a lens haptic onto or to an optical portion of the lens. The haptics can thus be brought into a defined position such that, when folding and ejecting the lens from the injector, they can be rolled in a defined manner into the optical portion of the lens so as to guarantee insertion and unfolding of the lens in the eye in the most reproducible manner possible.

21 Claims, 23 Drawing Sheets

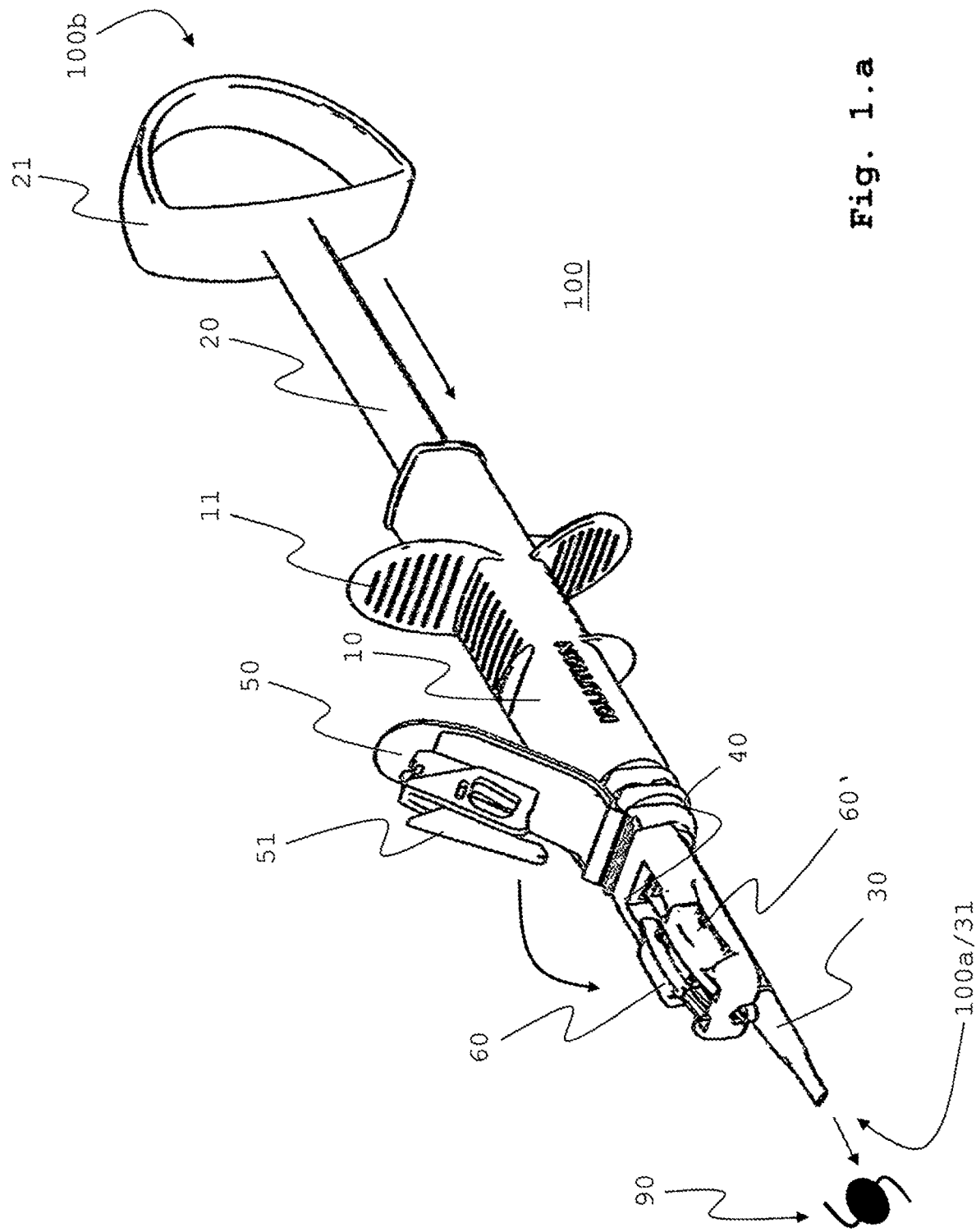
Fig. 1.a

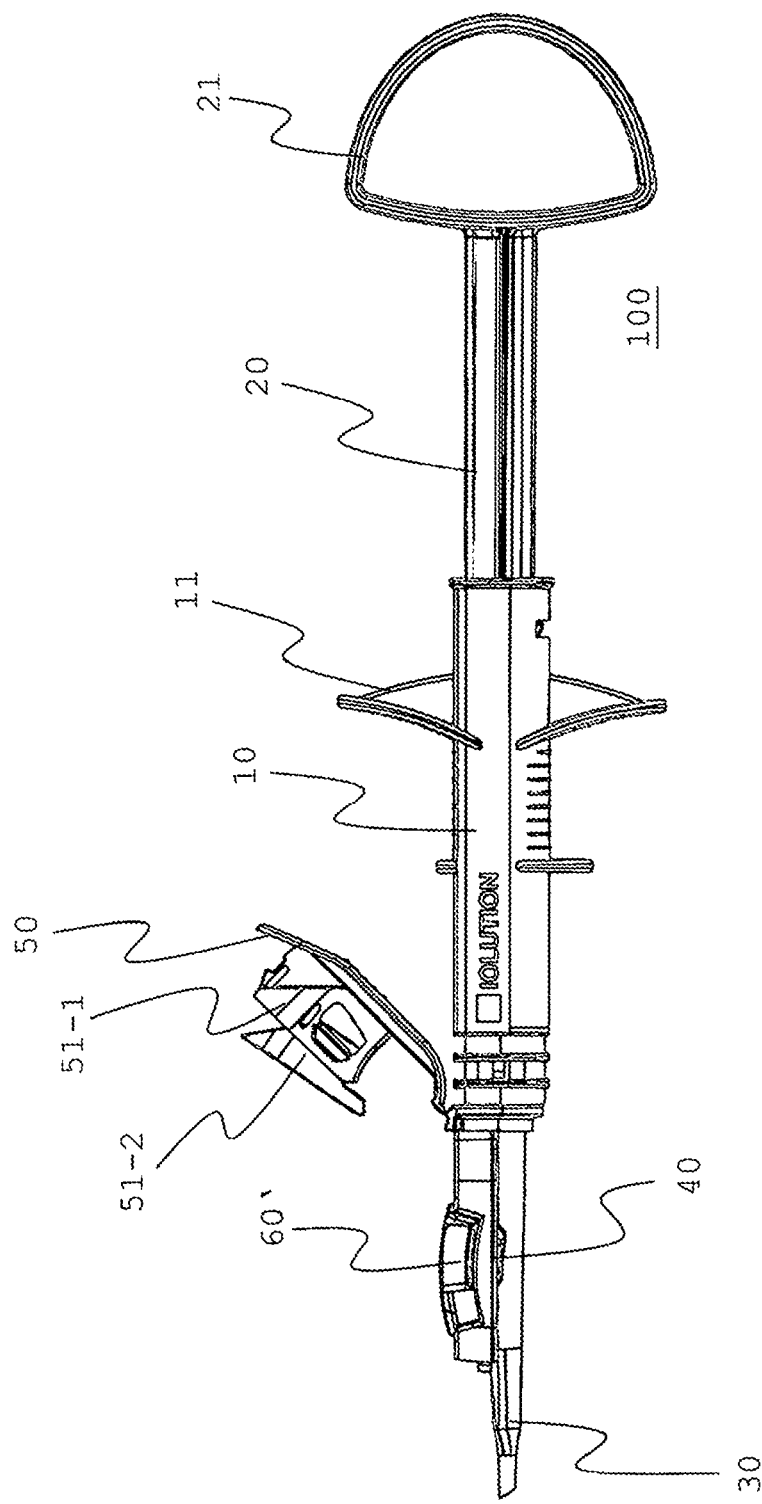
Fig. 1.b

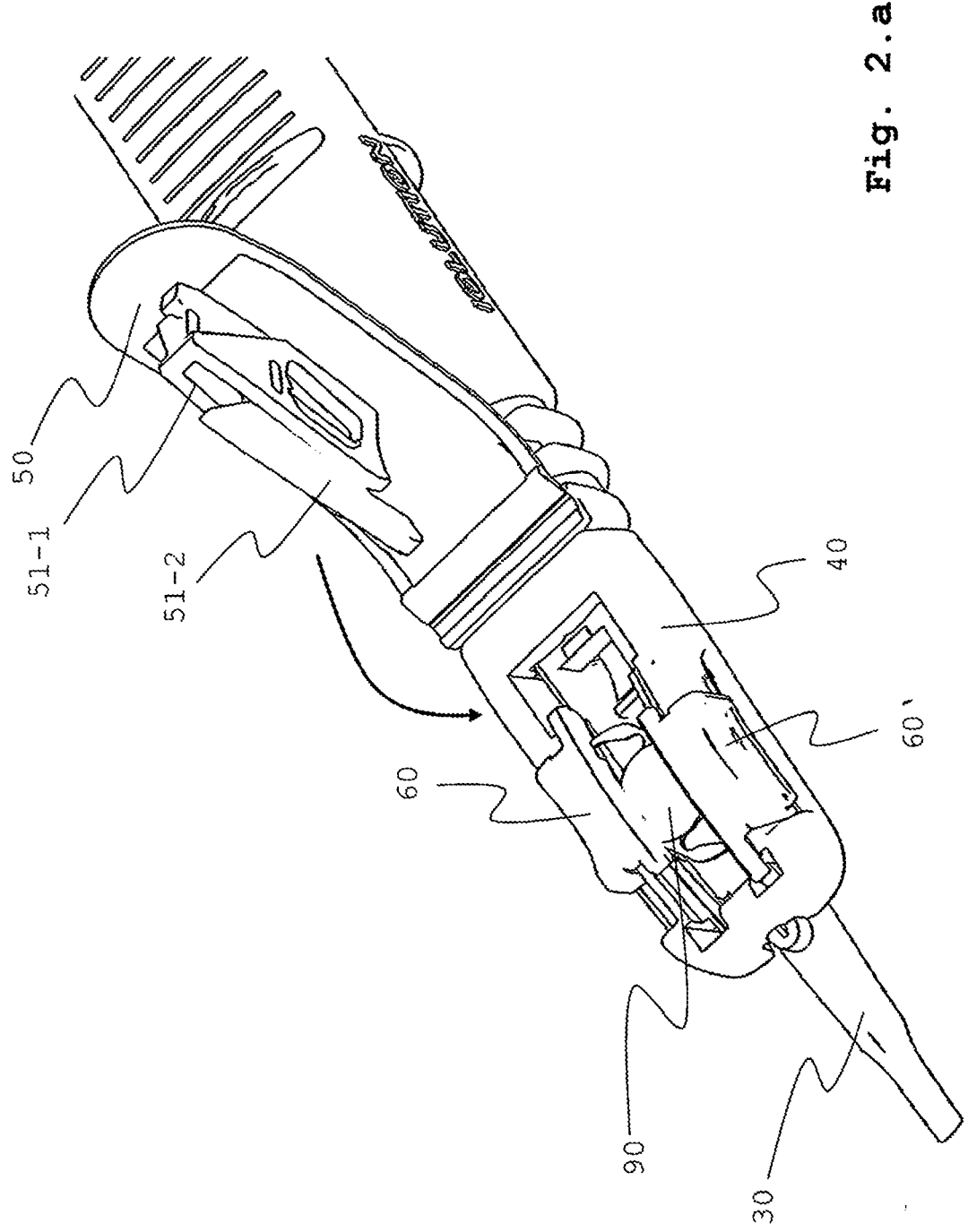
Fig. 2.a

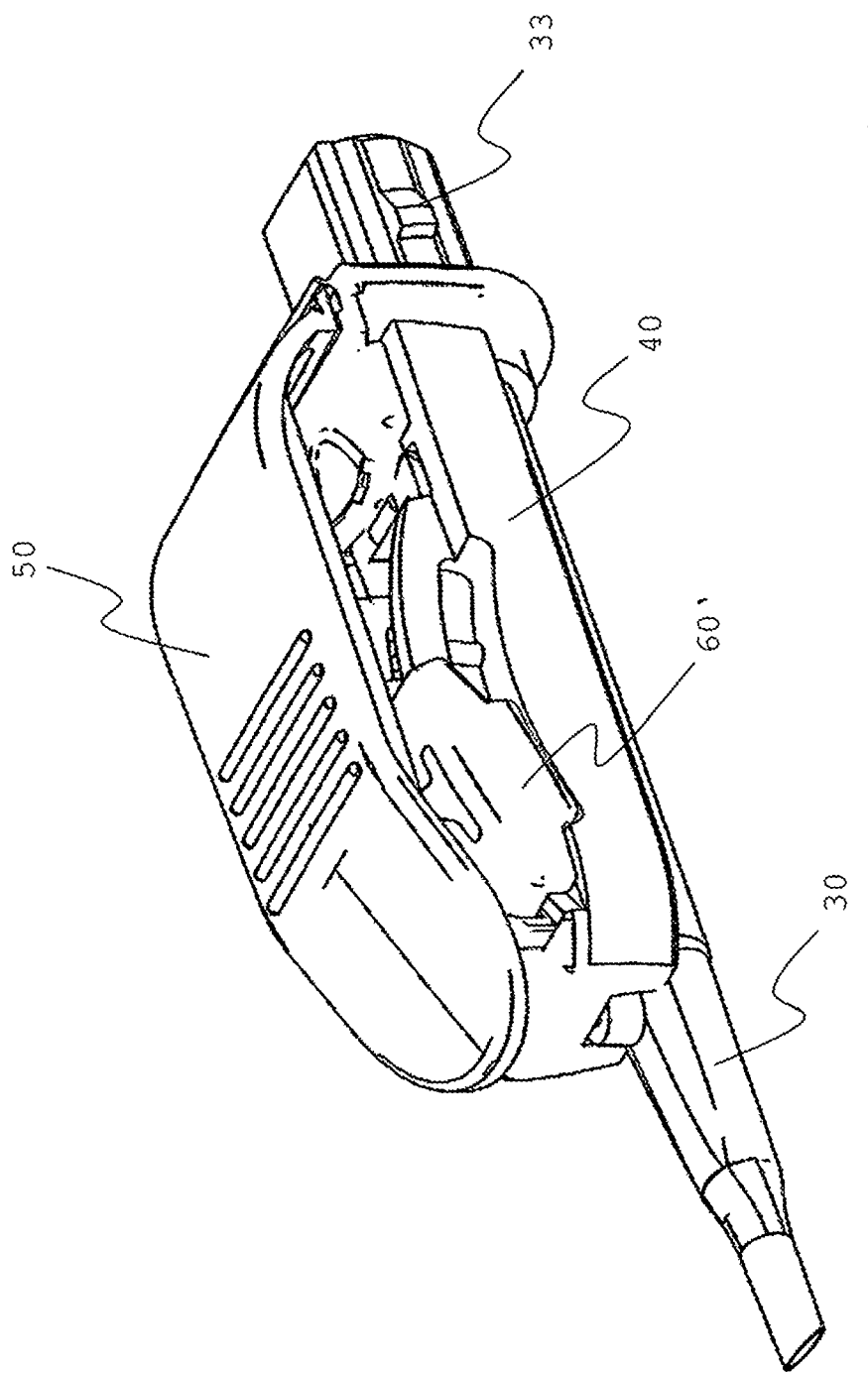

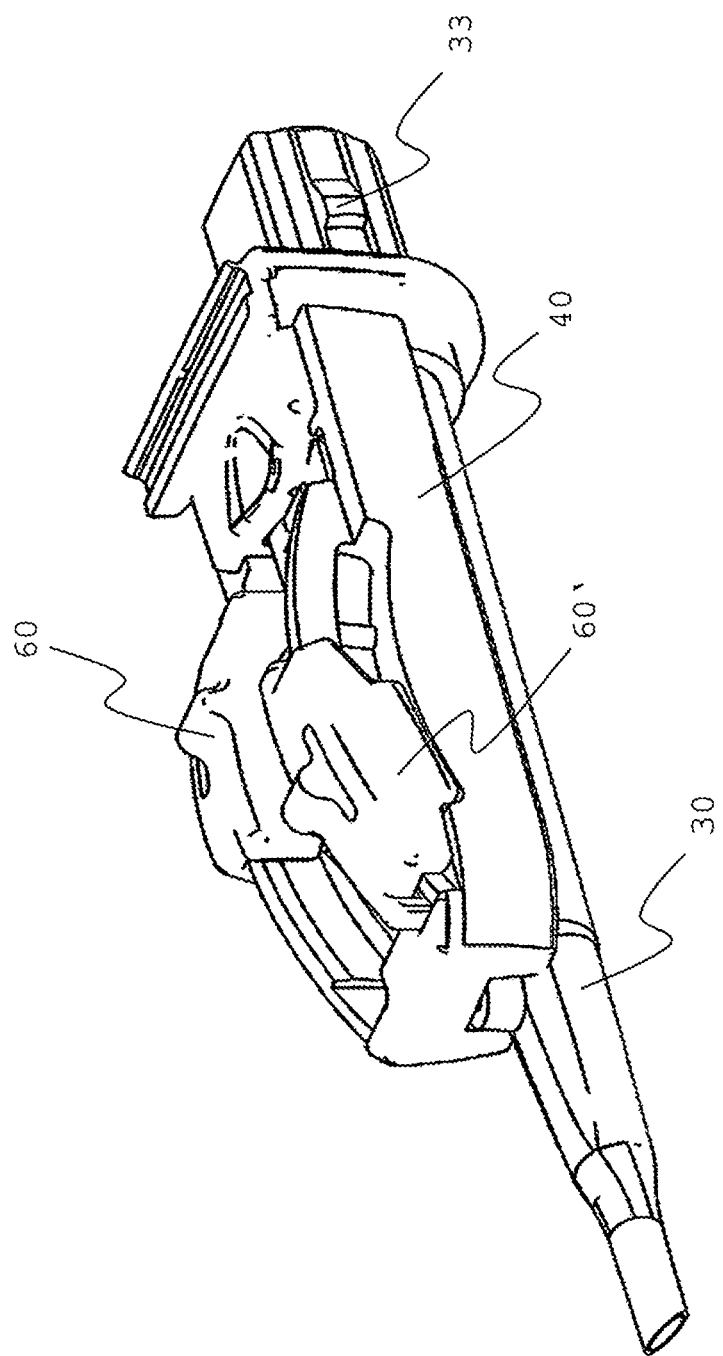
Fig. 2.c

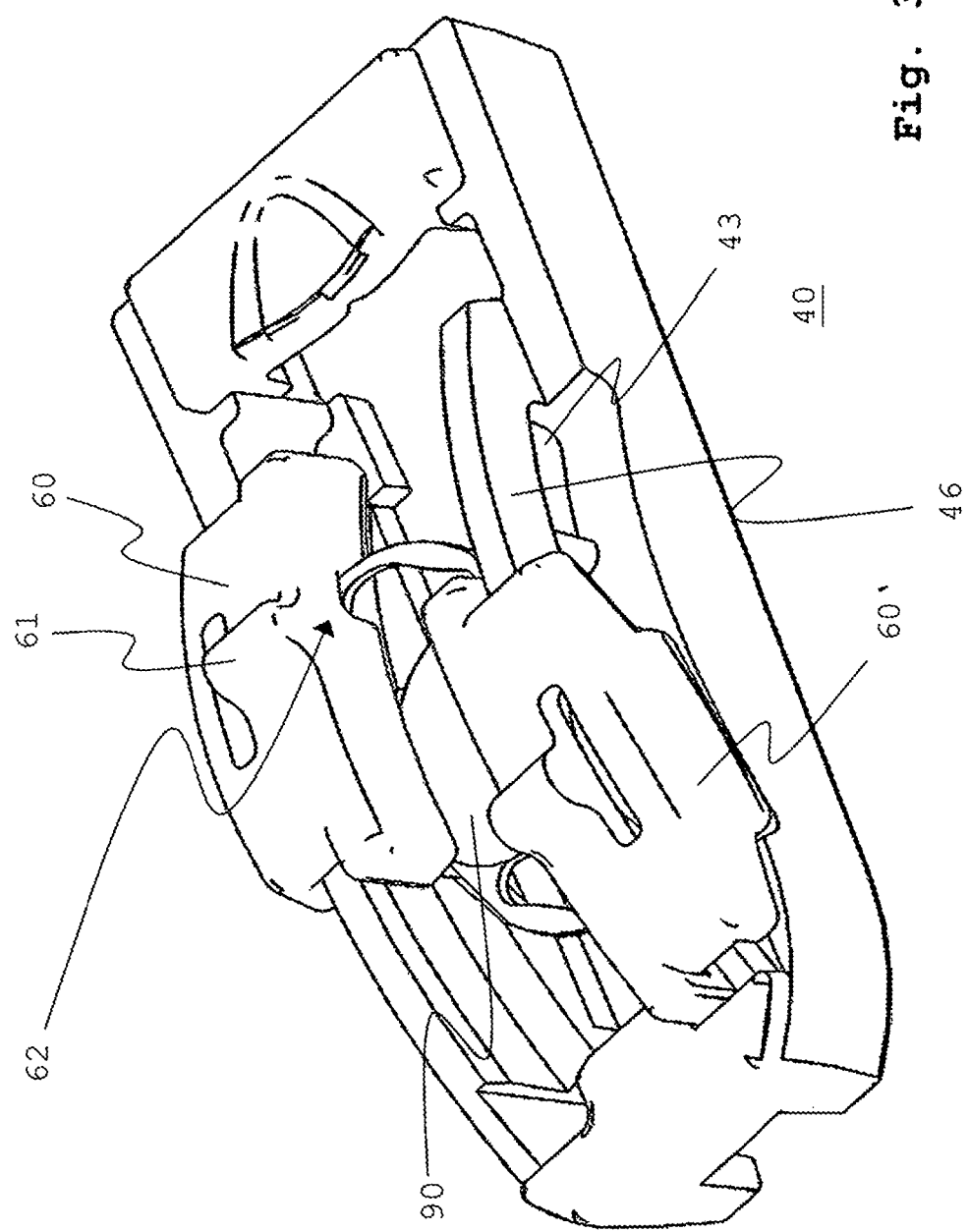

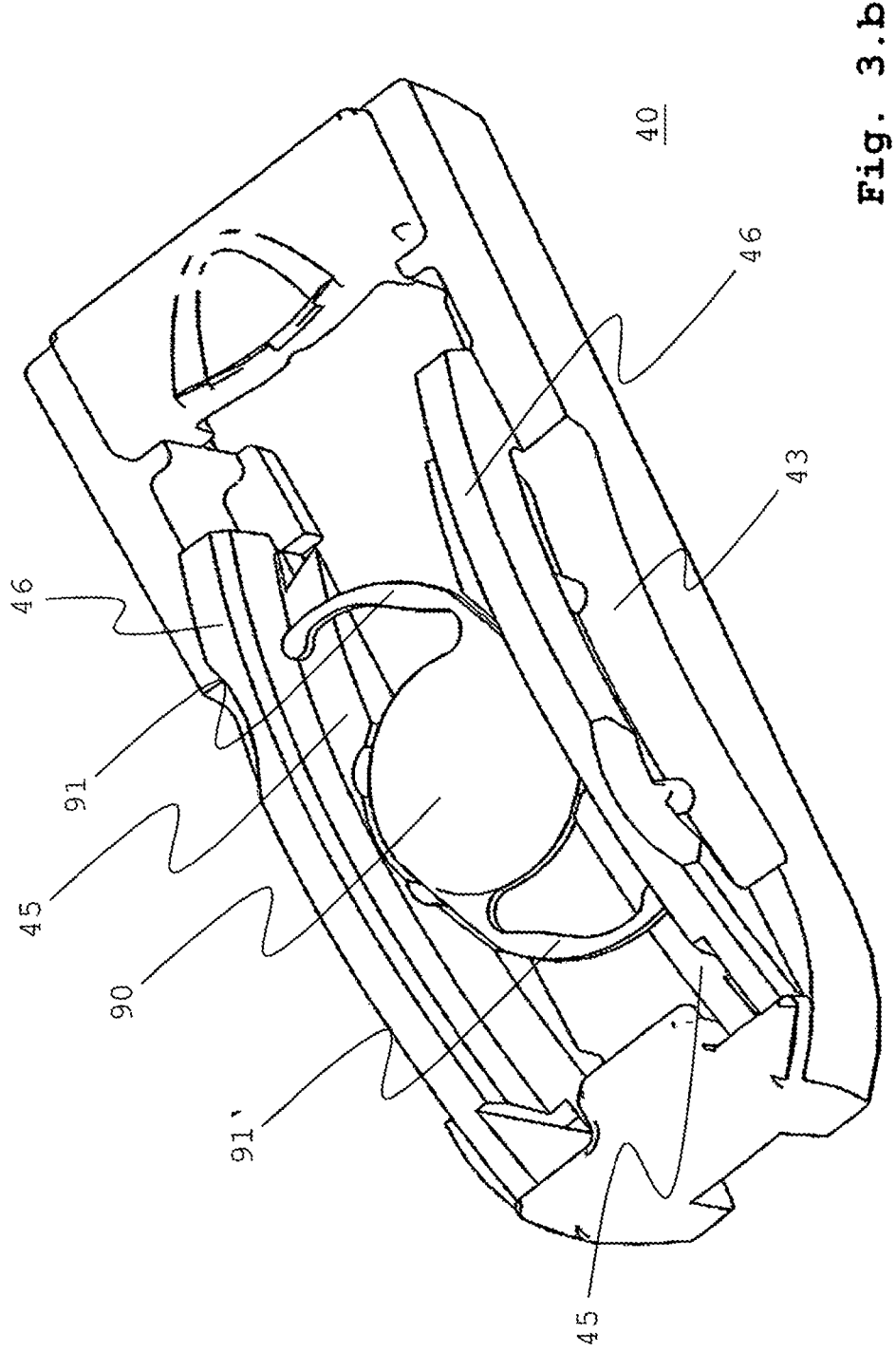
Fig. 3.b

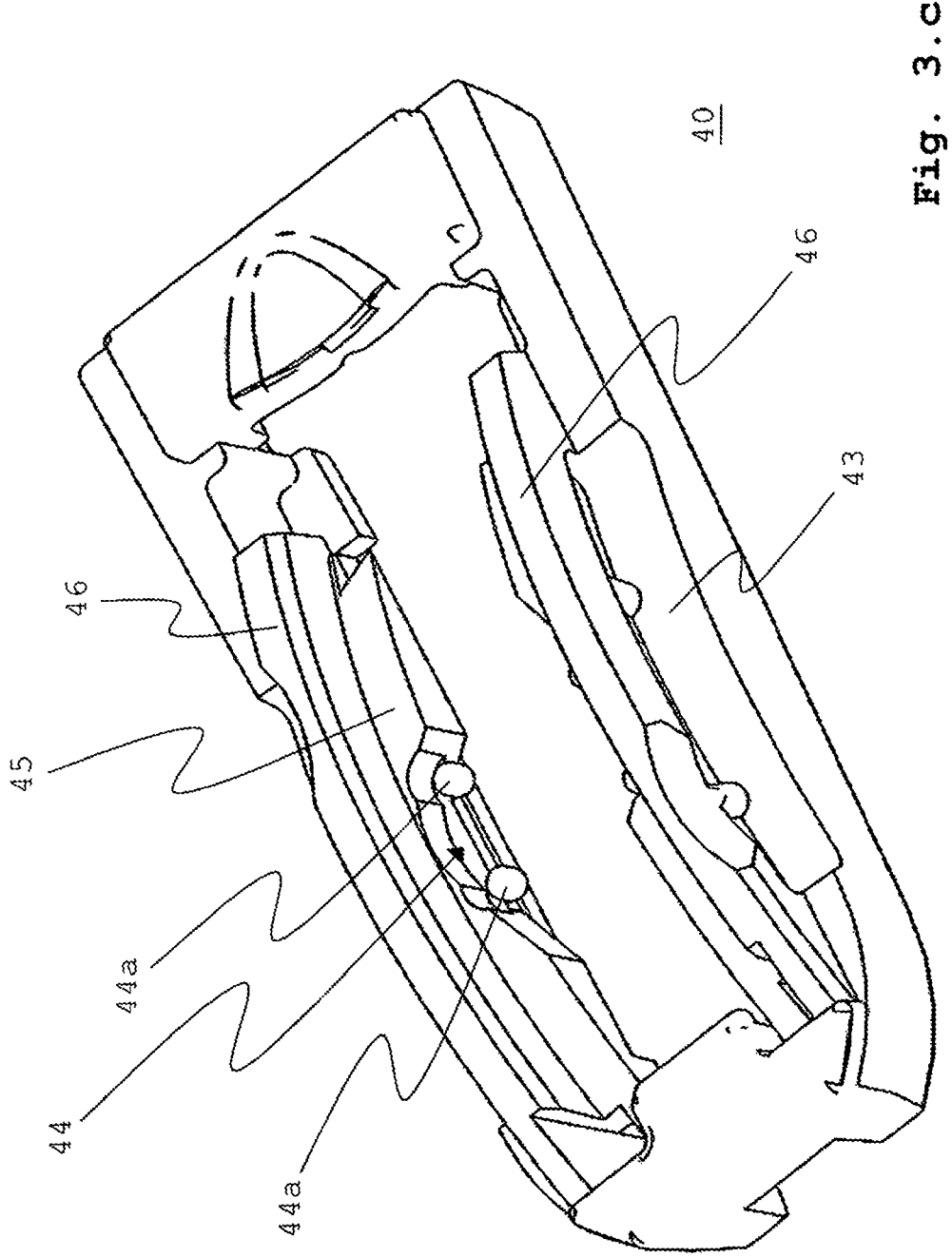
Fig. 3.c

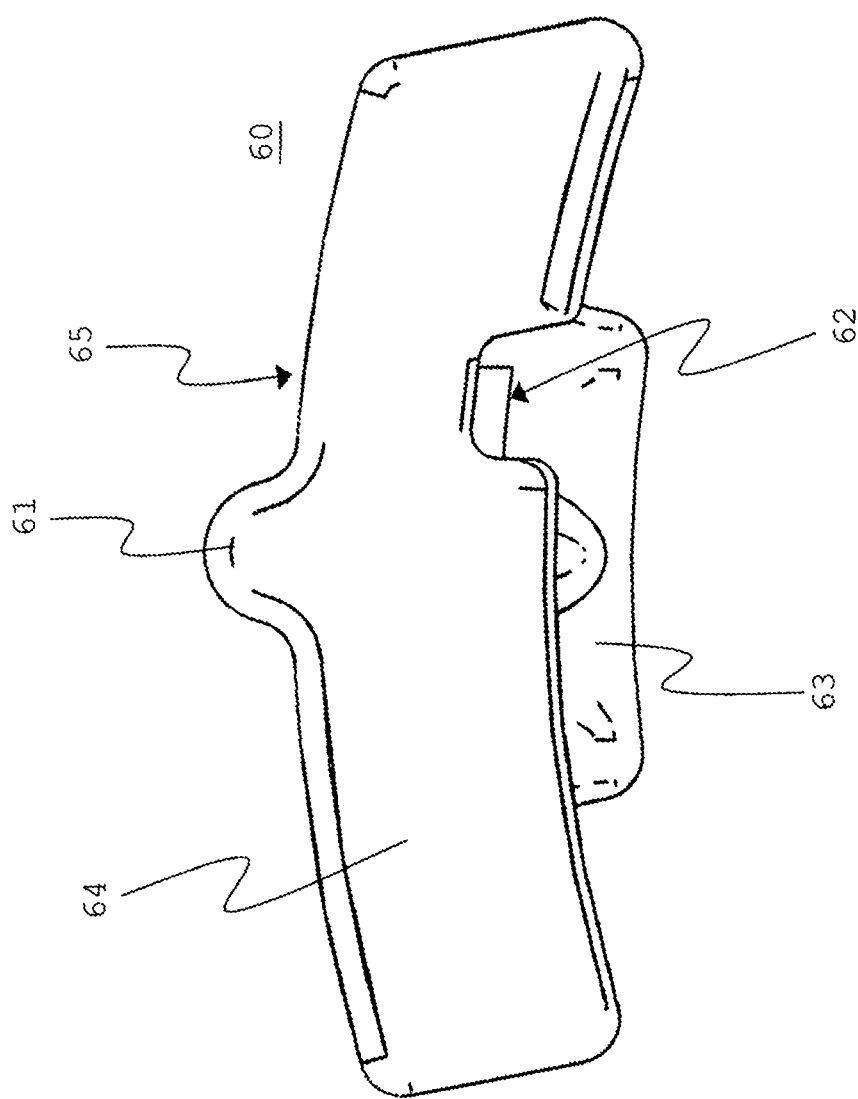
Fig. 4.a

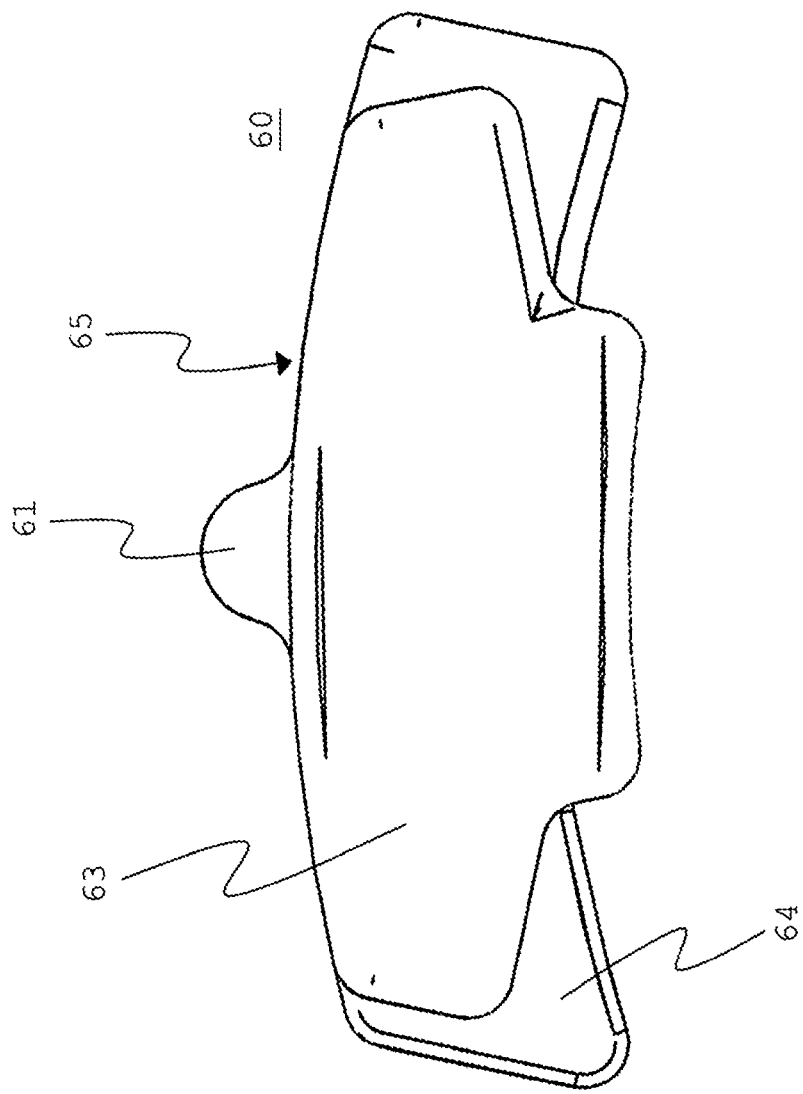

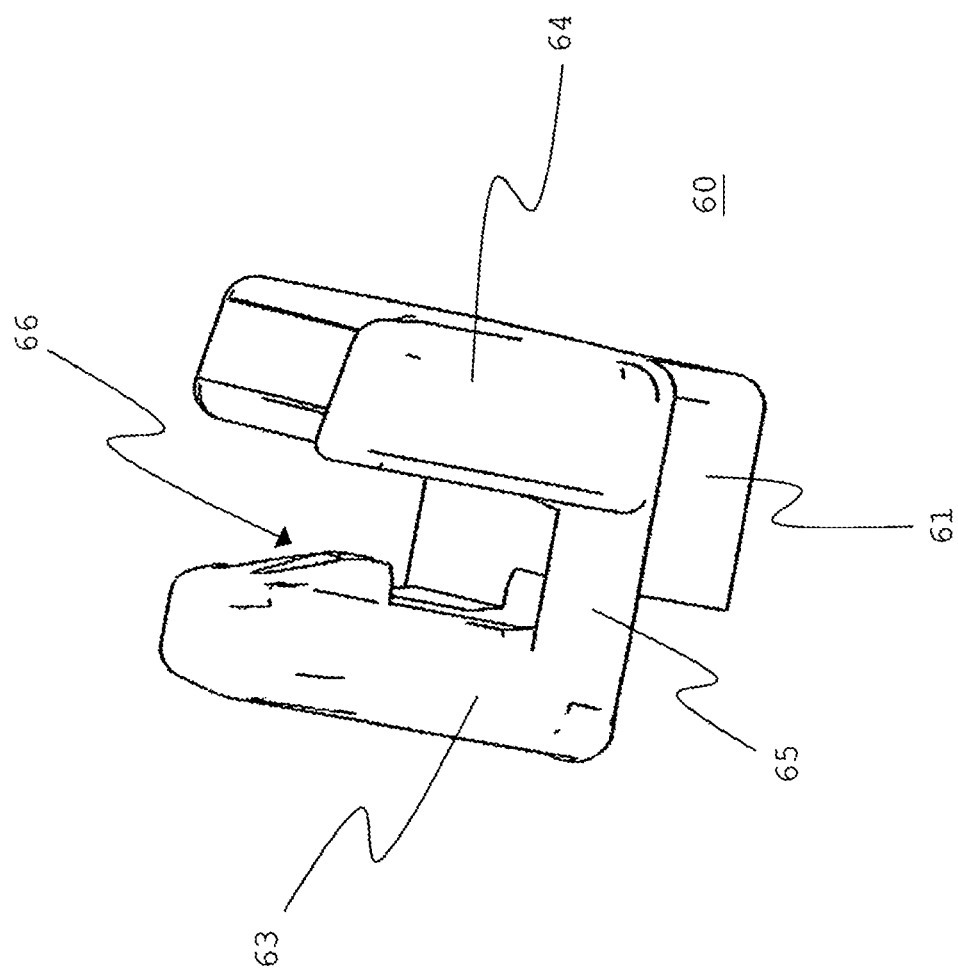
Fig. 4.c

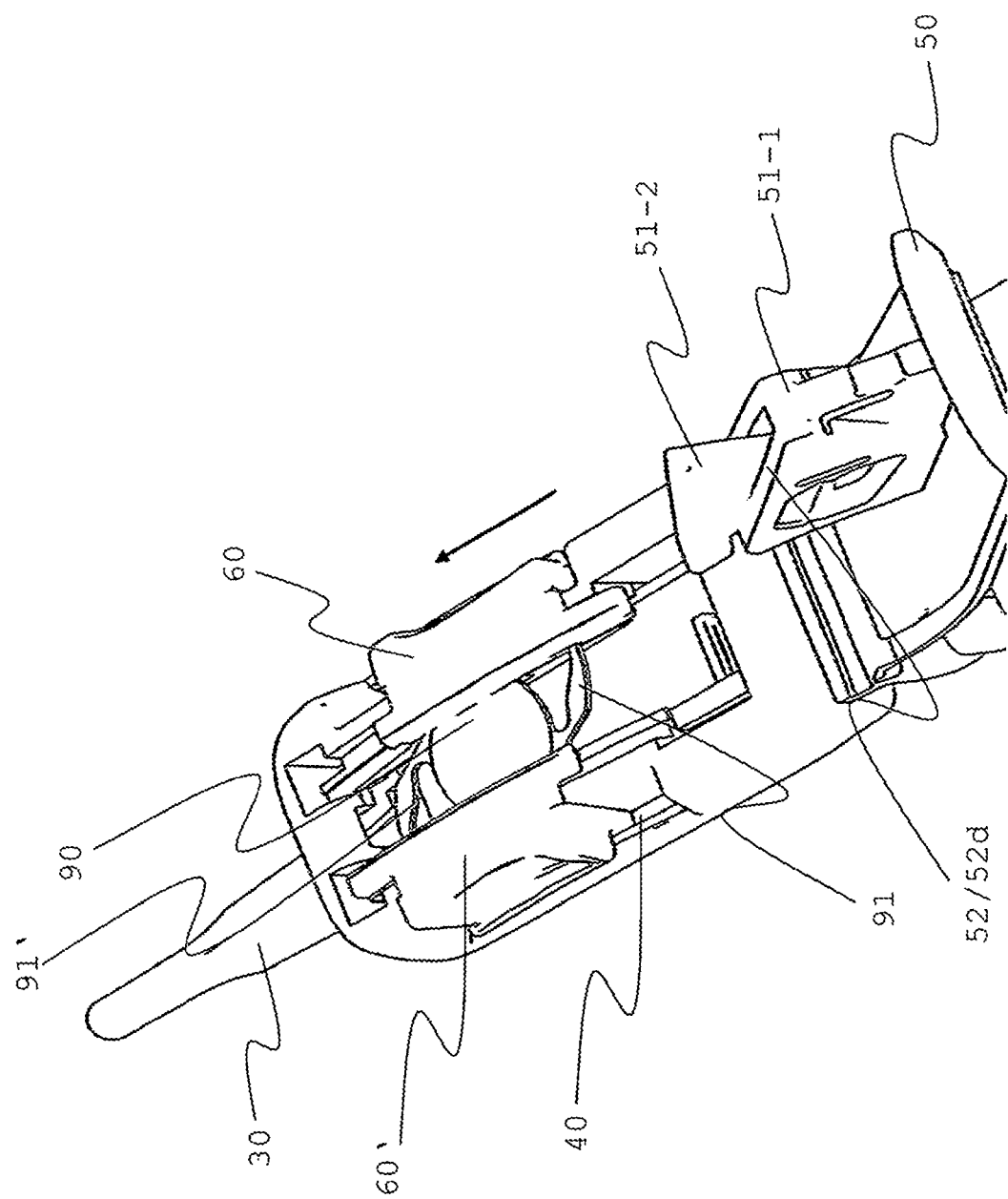

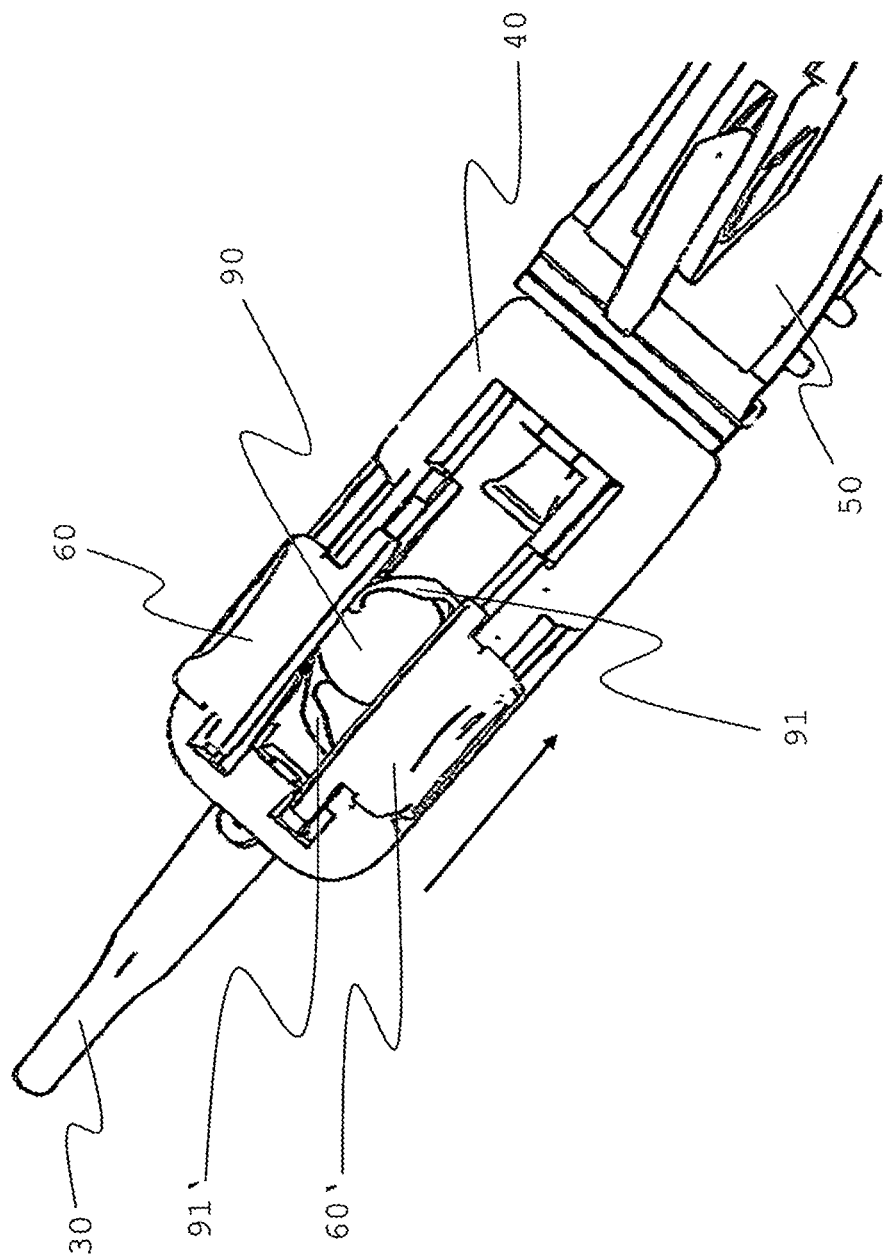
Fig. 5.b

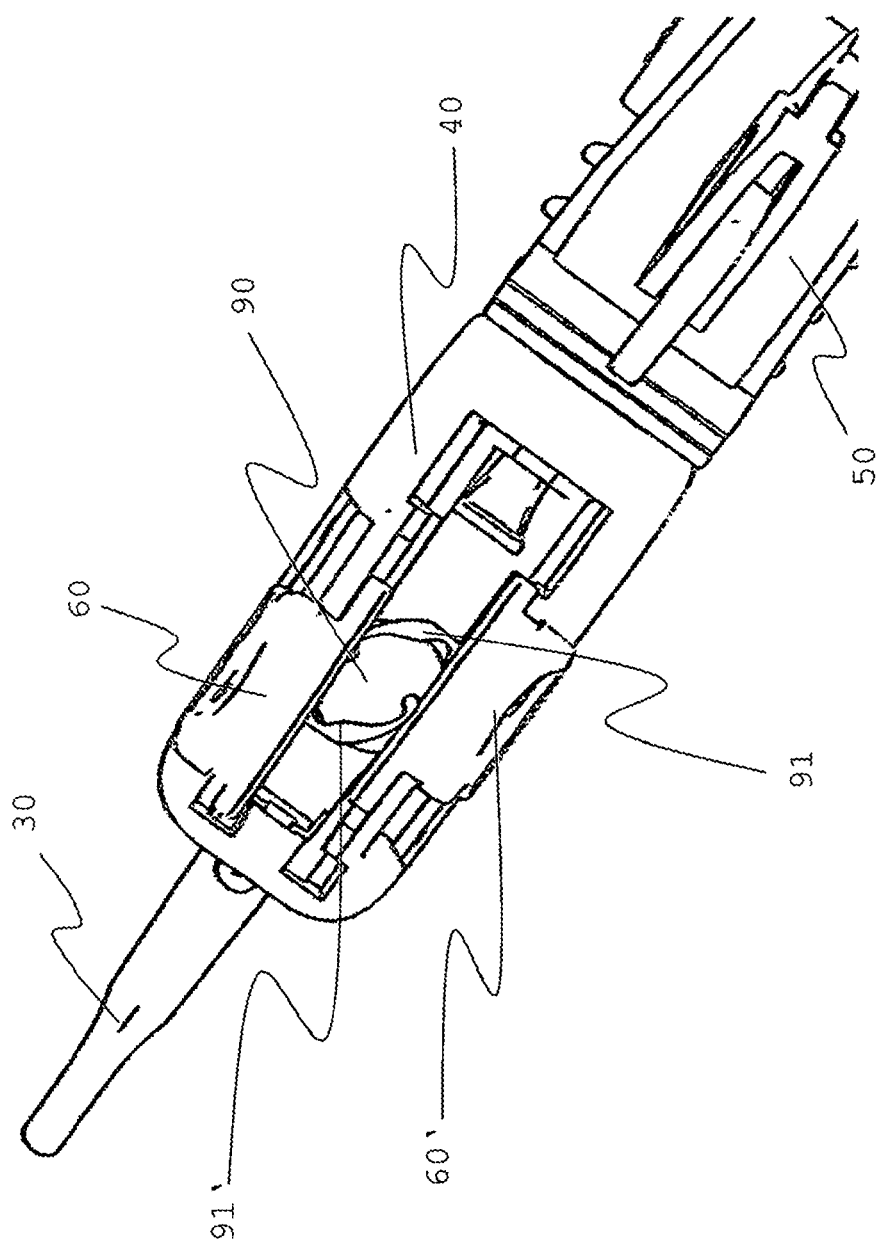
Fig. 5.c

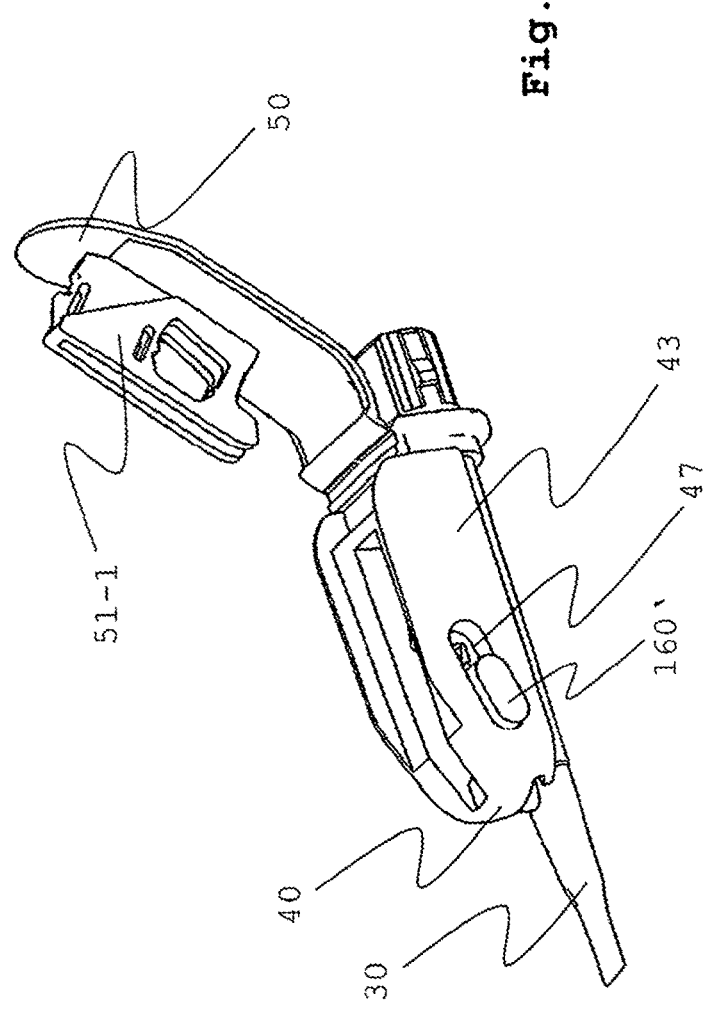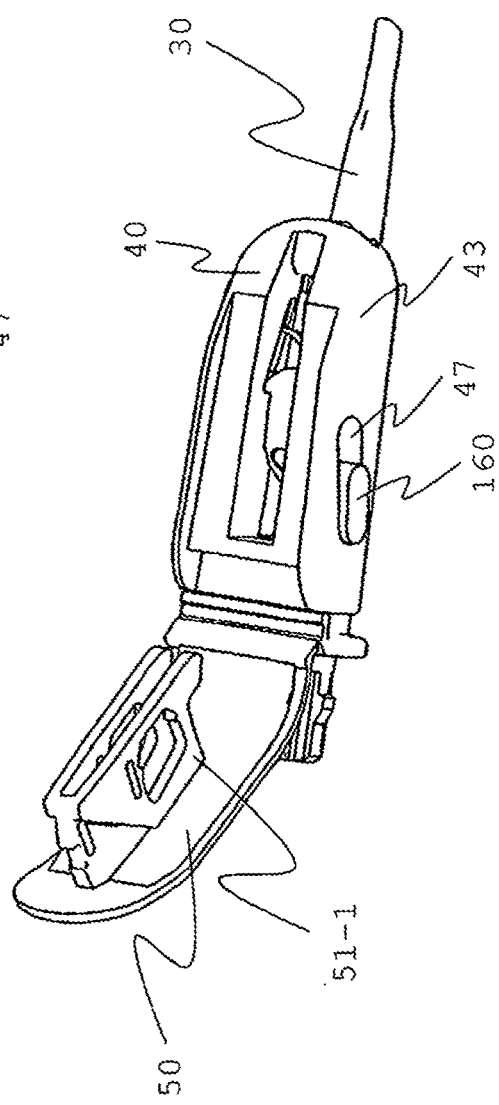

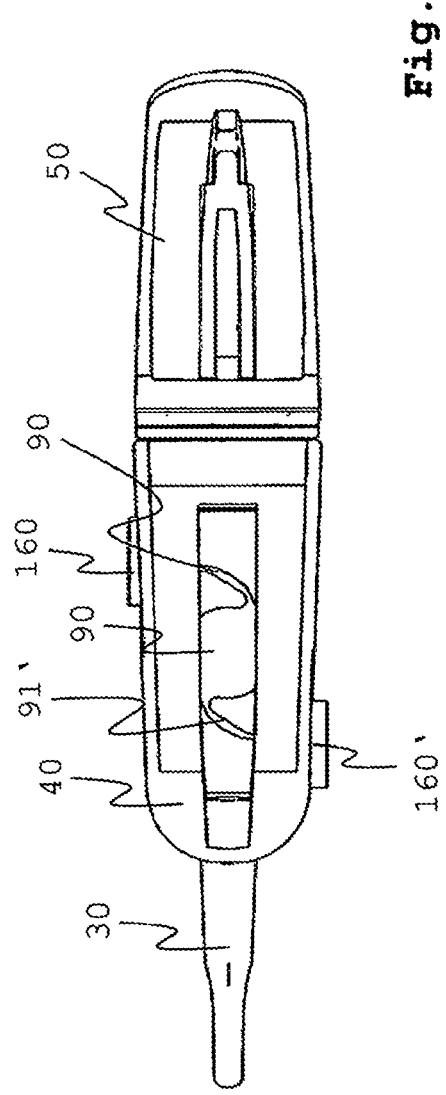
Fig. 6.c
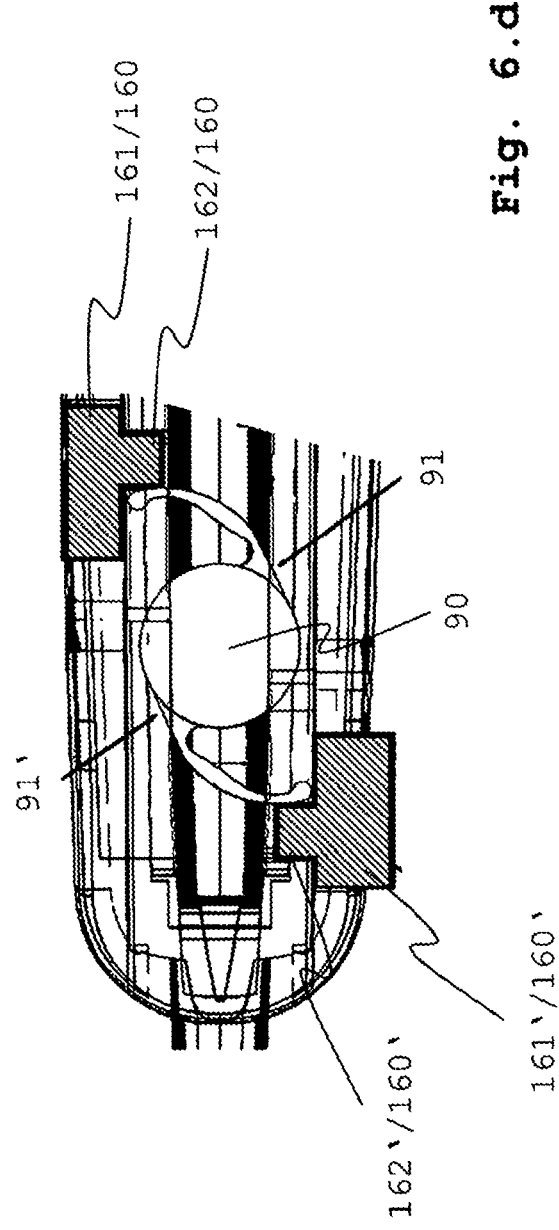
Fig. 6.d

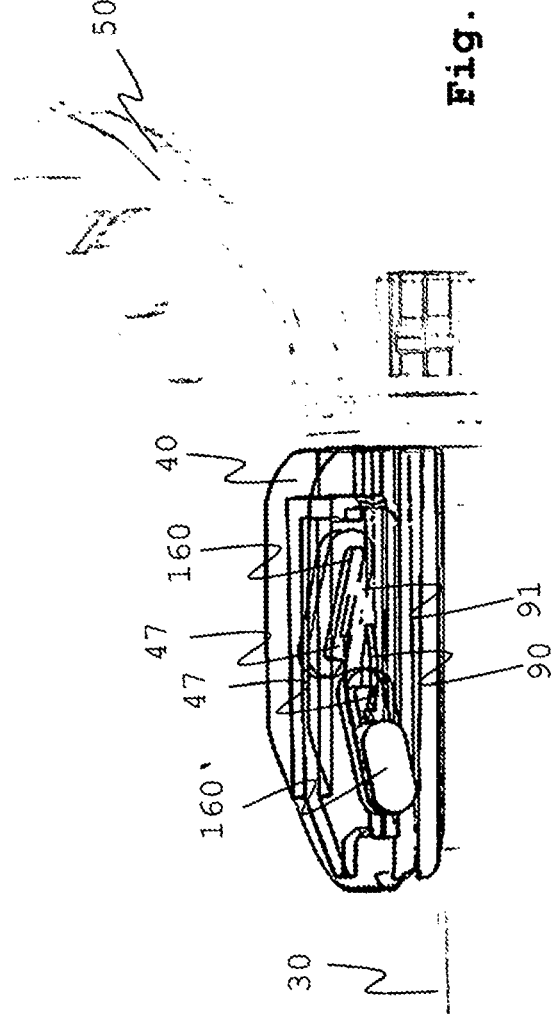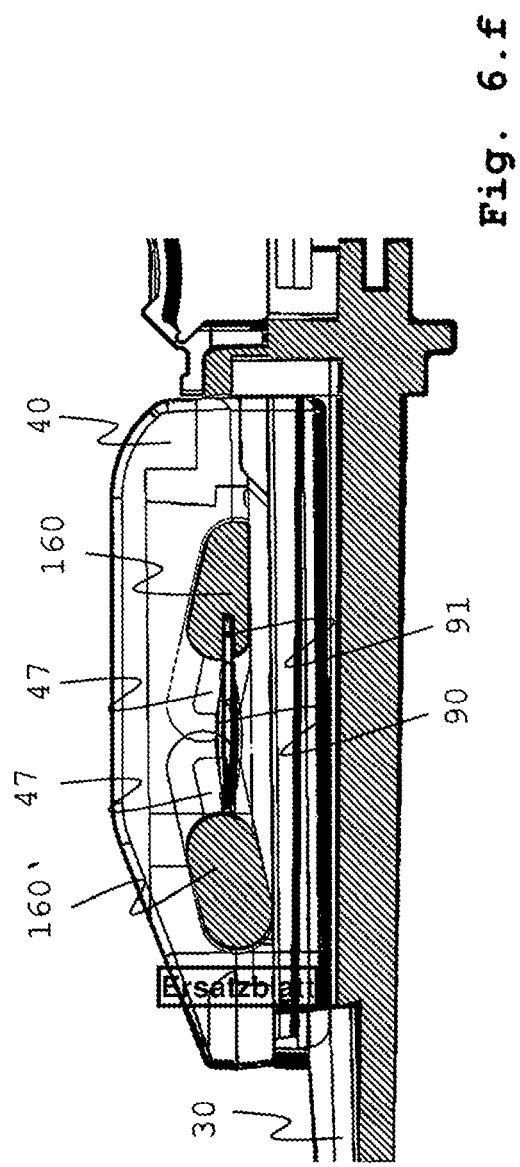

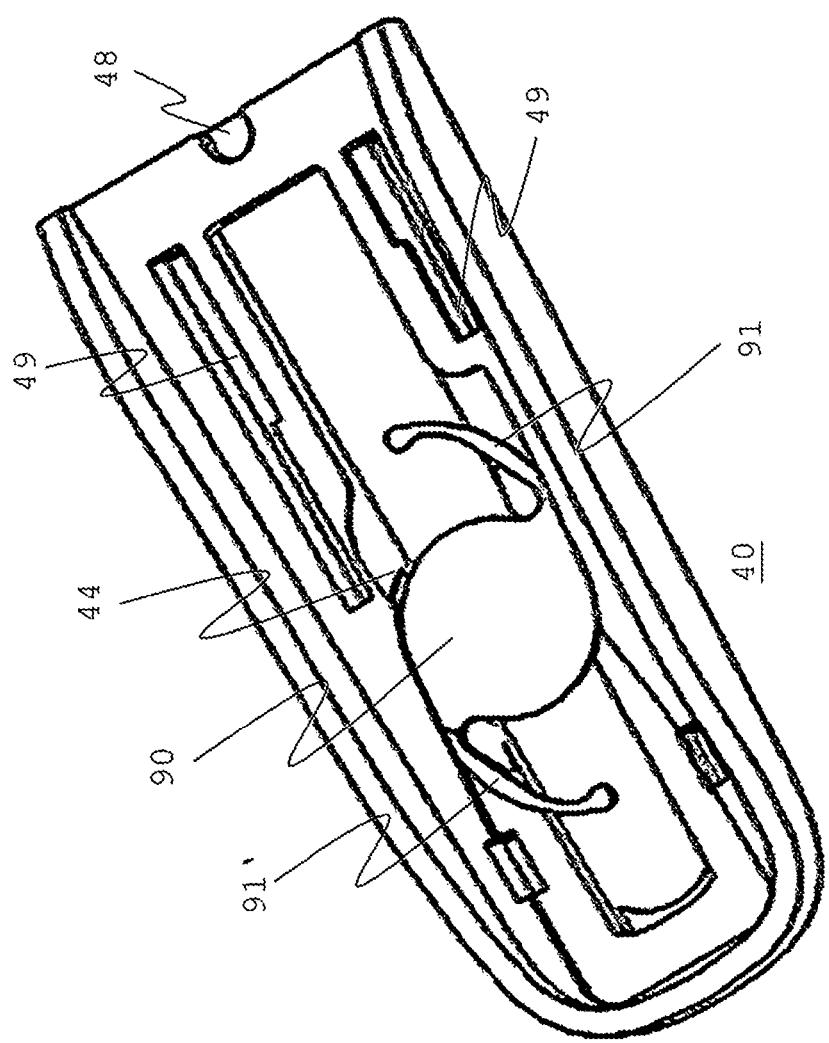

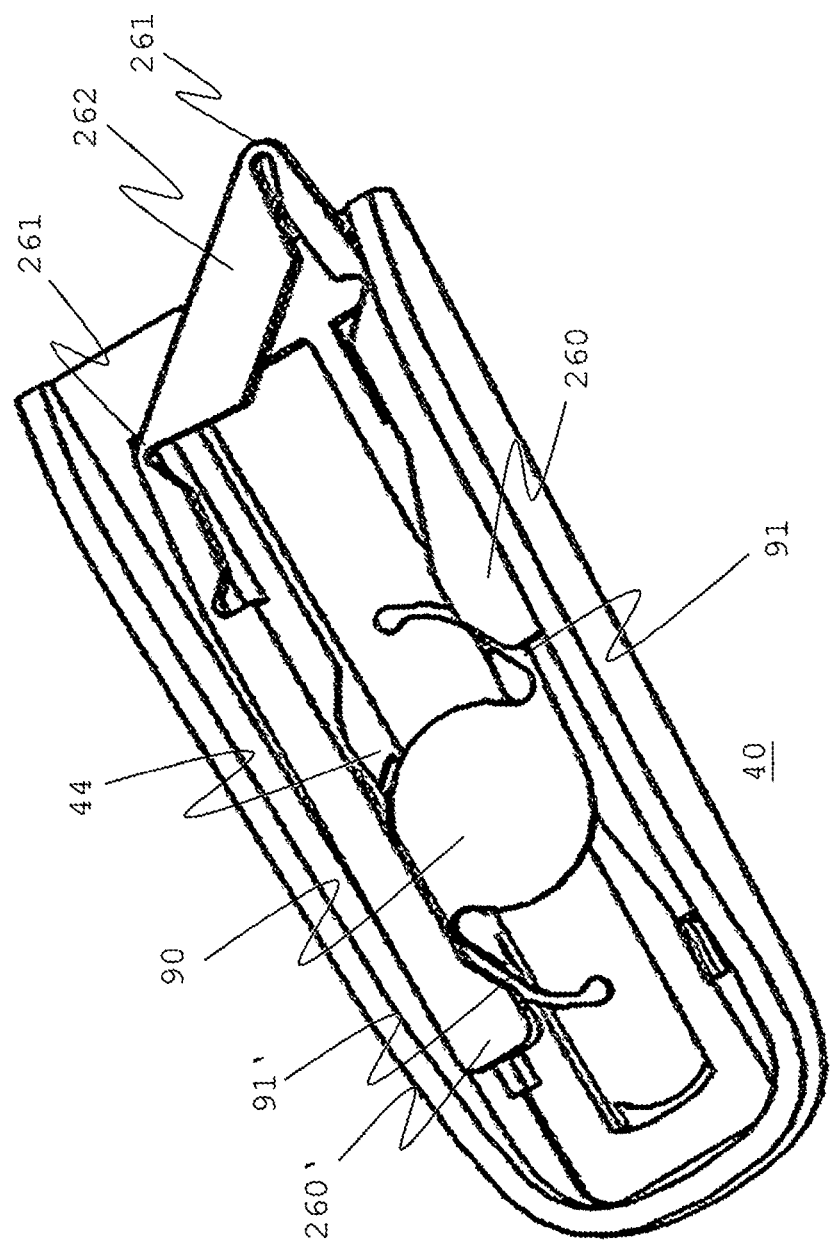
Fig. 7.b

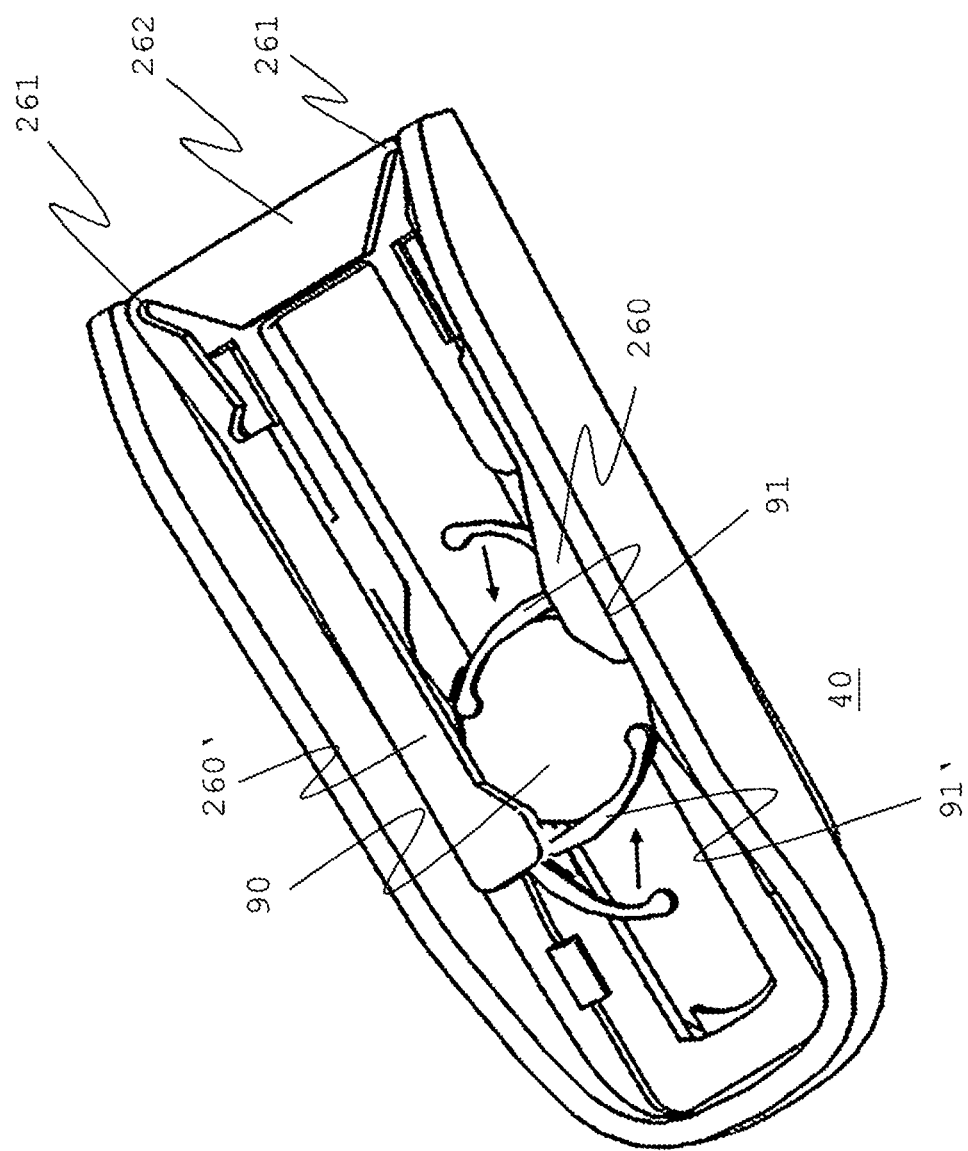
Fig. 7.c

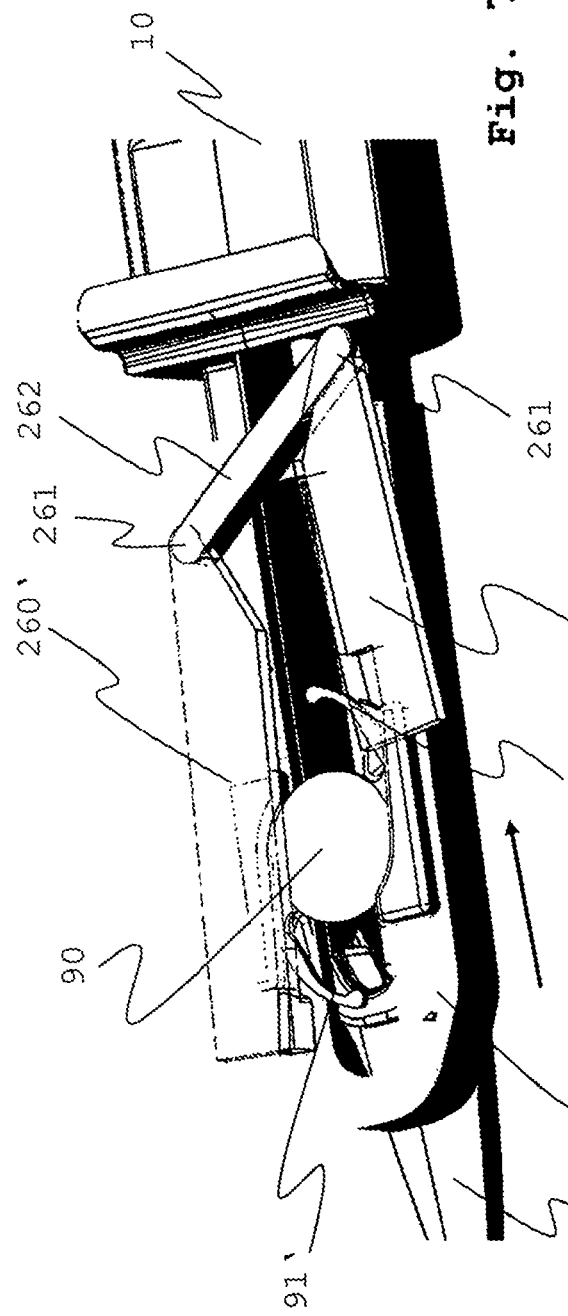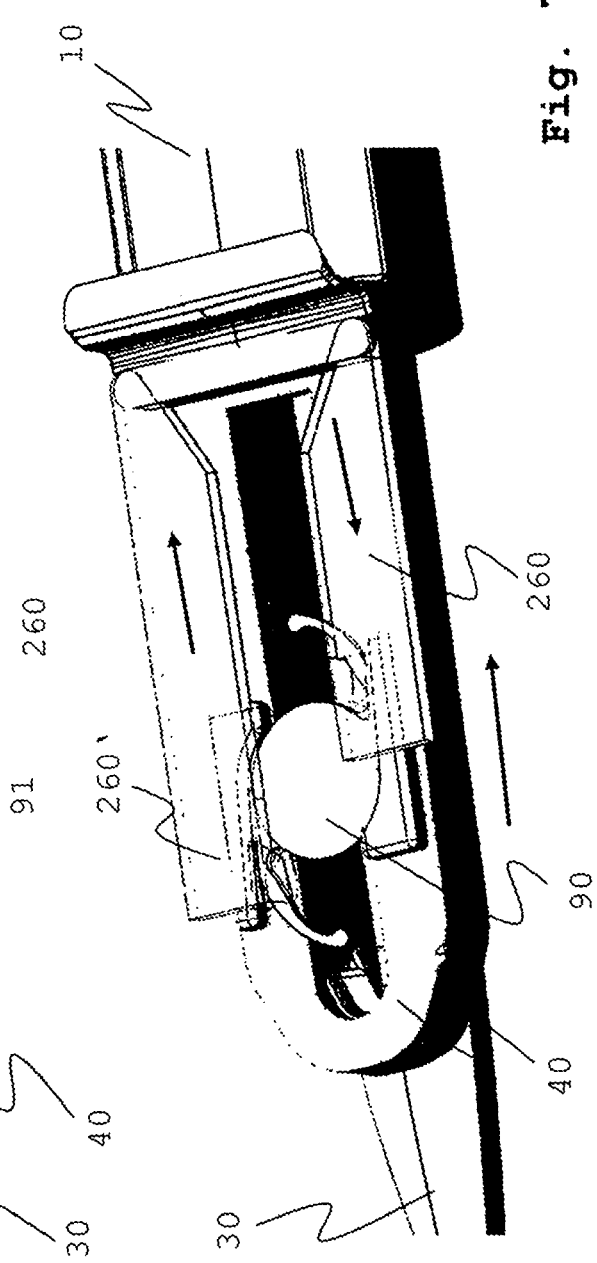

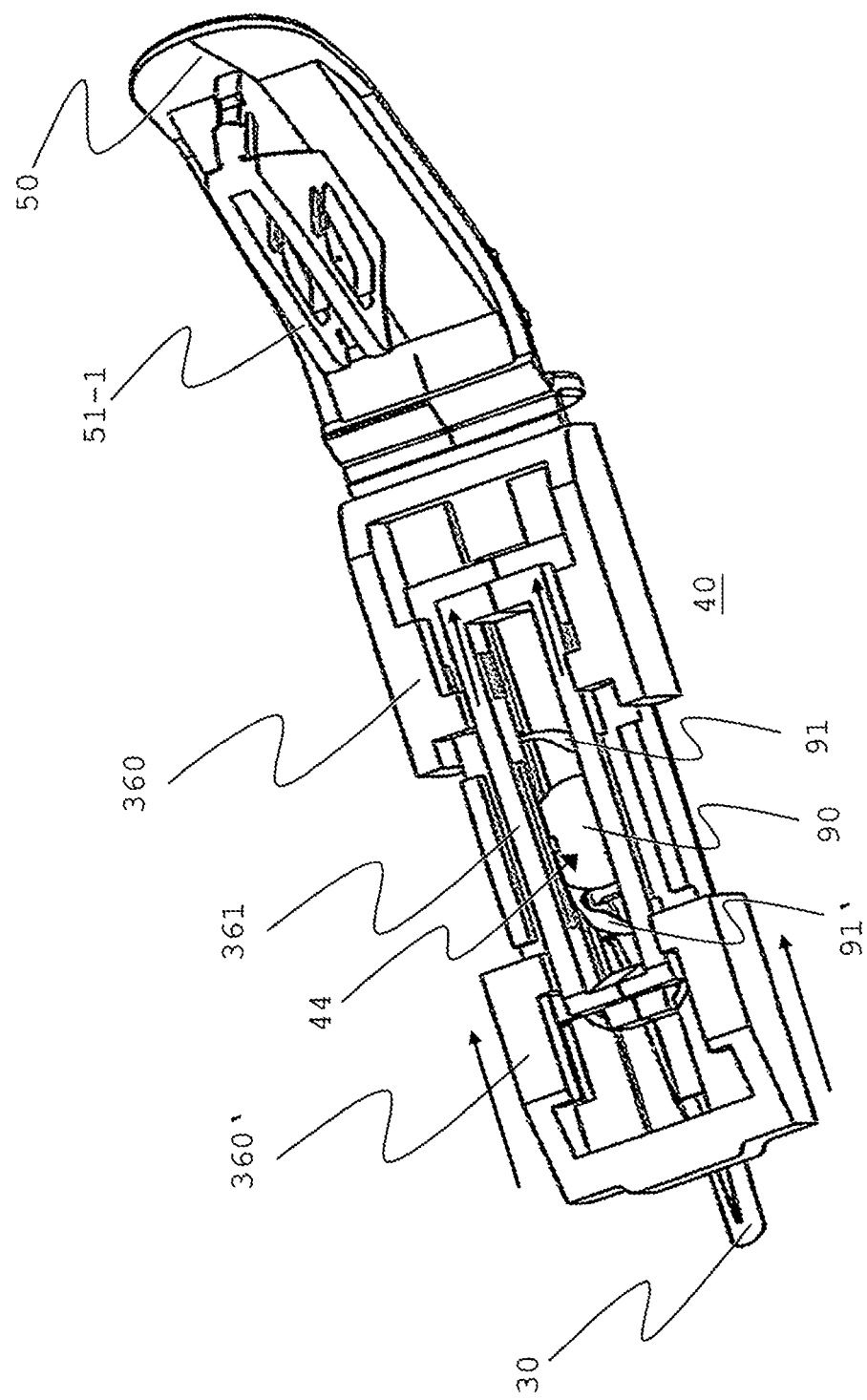
Fig. 8.a

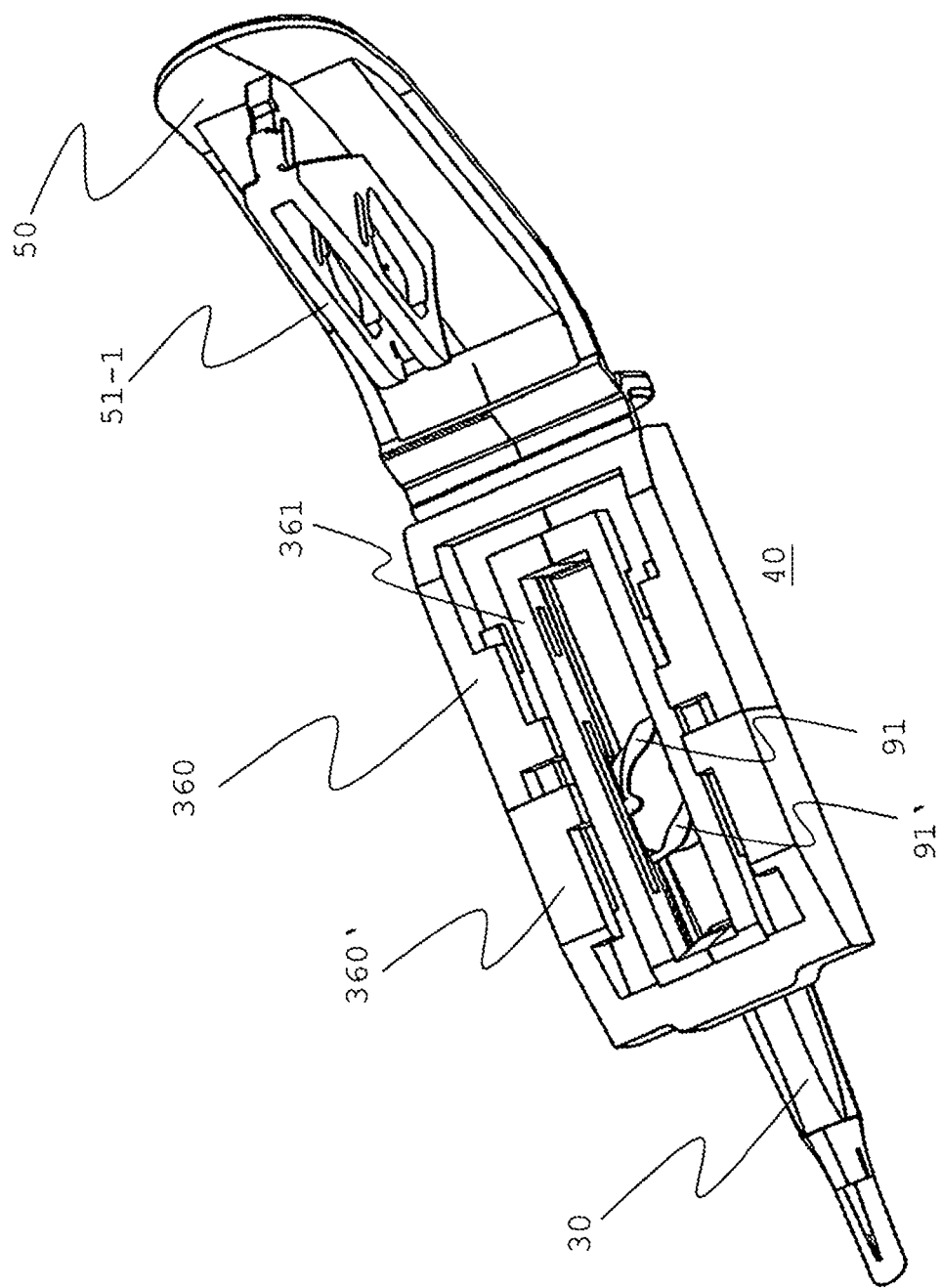

CARTRIDGE FOR AN INJECTOR FOR IMPLANTING AN INTRAOCULAR LENS

CROSS-REFERENCE TO RELATED APPLICATIONS

This application is a National Stage of International patent application PCT/DE2017/000193, filed on Jul. 5, 2017, which claims priority to foreign German patent application No. DE 10 2016 008 195.3, filed on Jul. 7, 2016, the disclosures of which are incorporated by reference in their entirety.

FIELD OF THE INVENTION

The present invention relates to a cartridge for an injector system for implanting an intraocular lens into an eye.

BACKGROUND OF THE INVENTION

Intraocular lenses are lens implants or artificial lenses to replace the natural lens of a human eye. They are in particular used to replace the lenses of an eye affected by cloudiness (cataract) of the lens. The affected lenses are removed by surgery, and the intraocular lenses are inserted. Insertion into the eye is accomplished by means of a so-called injector, for example. It is important in this context that the surgical incision through which an intraocular lens is implanted is as small as possible (e.g. about 2.2 mm). This allows to ensure the fastest possible healing process without complication and possibly also avoids the need for suture.

In order to be able to implant intraocular lenses which generally have a diameter of about 5 to 6 mm, the lenses must be foldable so that they can pass through the small incision of about 2.2 mm.

An injector for folding and inserting a folded lens into a human eye is described in International patent application WO 00/45746 A1, for example. The content of this patent application is fully incorporated into the present patent application by reference. There, an injector is described for implanting or introducing a temporarily folded intraocular lens, which injector can be used to insert the folded lens into the lens capsule of the eye through an incision of the required size of about 2.2 mm in the eye.

In a so-called insertion opening, the non-folded lens lies flat on a support surface for being transported and is retained by a retaining rib extending longitudinally and centrally to the lens. The retaining rib is also used there for folding and inserting the lens into the transport channel.

The injector described there ensures safe implantation of an intraocular lens into a human and/or animal eye. However, the loading of the injector or the insertion of the intraocular lens into the injector can only be carried out shortly before surgery, by the operating ophthalmologist or a supportive surgical nurse.

However, in order to be able to accurately insert the intraocular lens into the eye, it is necessary for the lens to be positioned as precisely as possible on the support surface so that the lens can be precisely introduced into the transport channel by the folding rib.

If the lens is not loaded with sufficient accuracy, this may result in an undesired rotation of the lens during folding and insertion of the lens into the transport channel by means of the folding rib. Under certain circumstances, the lens may even become jammed between the folding rib and the transport channel, rendering it unusable.

Therefore, the loading done by the ophthalmologist or surgical nurse presents a potential risk. Moreover, the lens previously stored in a package under sterile conditions may become contaminated when being removed from the package and placed in the injector.

A further development of the injector described above is disclosed in International patent application WO 2012/155887 A1. The content of this patent application is fully incorporated into the present patent application by reference. Here, the lens can be stored in the injector already in advance. Retaining of the lens and folding of the lens is accomplished by two separate components in this system.

In order to allow to introduce an intraocular lens into the eye in the most reproducible and precise way, it has been found that not only the position and folding of the lens as such is important, but also the position of the haptics relative to the optical portion of the lens during folding and upon ejection of the lens from the injector.

In order to be able to position the haptics in a defined manner, the cited patent application already describes a haptic slider which, once the lenses have been folded and inserted into the transport channel, is used to bring the rear haptic into a defined position with respect to the lens. In more detail, the rear haptic is introduced into a rear receiving region of the folding body. Furthermore, the folding body has an abutment for a front haptic of the lens. Upon initial advancement, the abutment is then effective to place the haptic on the lens. During further advancement of the lens within the transport channel, the lens is rolled. In particular, the haptics are preferably intended to be wrapped into the optical portion of the lens.

SUMMARY OF THE INVENTION

Given the background described above, it is an object of the present invention to provide an injector for intraocular lenses, which provides for improved behavior of the lens during the folding and ejecting of the lens from the injector.

In particular, when the lens is ejected from the injector, the haptics shall already be wrapped in defined manner in the optical portion of the lens in order to ensure the safest possible and reproducible introduction of the lens into and deployment in the eye.

These objects are already achieved by a cartridge according to independent claim 1. Advantageous embodiments can be found in the subject matter of the dependent claims, the description, and the figures.

Generally, the invention proposes to improve the injector described in the prior art such that one or more, preferably two, haptic sliders are provided directly on the cartridge.

In detail, the present invention provides a cartridge for an injector system for implanting a lens into an eye, which comprises a receiving region for at least one lens and at least one movable haptic slider for moving a lens haptic within the cartridge, preferably for displacing or sliding a lens haptic onto and/or to an optical portion of the lens. The haptic and/or haptic tip applied thereon or thereto can contact the optical portion of the lens or a peripheral area of the lens. The cartridge is in particular intended for an injector system that comprises a folding body.

By means of the at least one haptic slider, a haptic can be transferred into a defined position so that it can assume a defined position during the subsequent wrapping into the optical portion of the lens induced by the folding and the advancement, and when being unfolded in the eye.

The cartridge provides a region or a lens chamber for holding or storing the lens and, when required, for loading the injector. The receiving region for the lens in the cartridge is in particular distinguished by the fact that the lens or at least the optical portion of the lens can be stored or arranged there in a substantially stress-free manner, preferably flat. In an alternative, the lens may also be positioned in an already pre-folded state in the receiving region.

In particular, the haptic slider comprises an outer portion which is guided on the outer surface of the sidewall of the cartridge, and an inner portion which is guided on the inner surface of the sidewall of the cartridge.

In one embodiment, the haptic slider does not only perform the function of moving, but also performs the function of a holder for the lens. In this embodiment, the cartridge is distinguished by the fact that the lens is captured or can be captured within the lens receiving region by means of the haptic slider. In particular, the lens is prevented from simply falling out of position.

For this purpose, the cartridge and the haptic slider are preferably adapted such that at least a portion of the lens is captured within the receiving region by the haptic slider, in particular by the inner portion of the haptic slider, both in the initial state and in the advanced state thereof. For example, a peripheral area of the optical portion of the lens is covered by the haptic slider.

The haptic slider preferably provides a driver for a haptic tip of a lens haptic in order to be able to displace the haptic. In one embodiment of the cartridge, the driver is provided by a recess in the inner portion of the haptic slider.

The haptic slider is in particular mounted to the cartridge so as to be movable, preferably by a snap-in connection. In one embodiment, the haptic slider is arranged on and preferably snap-fitted to or latched into a sidewall and/or a bottom of the cartridge so as to be displaceable substantially axially. In one embodiment, the outer portion of the haptic slider is latched to the outer surface of the cartridge sidewall. In another embodiment, the haptic slider is mounted to a sidewall of the cartridge and extends into the cartridge through an opening in the sidewall of the cartridge.

Preferably, the head portion or an outer portion of the haptic slider is guided on the top of the sidewall or directly on the sidewall of the cartridge. For better handling of the haptic slider, a projection may be formed on the head portion of the haptic slider or on the outer portion of the haptic which extends through the sidewall. It serves as a grip surface for a finger.

In one embodiment, an intraocular lens has two haptics. Therefore, preferably, two haptic sliders are provided. The two haptic sliders are preferably displaceable in opposite directions.

To promote reliable and safe insertion of the lens into the eye, the haptics should not protrude from the lens. The haptics should rather be in a defined position. For example, they may or should be wrapped into the lens. Depending on the orientation of the lens in the injector, one haptic is located in the front portion (the front haptic) and one haptic in the rear portion (the rear haptic) of the cartridge, for example.

In one embodiment, the cartridge has a rear haptic slider associated with a rear haptic and a front haptic slider associated with a front haptic for this purpose. The rear haptic slider is arranged so as to be displaceable towards the front end of the injector, for displacing or sliding the rear haptic preferably onto and/or to the optical portion of the lens. The front haptic slider is arranged so as to be displaceable towards the rear end of the injector, for displacing or sliding the front haptic preferably onto and/or to the optical portion of the lens.

The two haptic sliders can be actuated one after the other or simultaneously, for example. In an alternative variant, the front and rear haptic sliders are coupled to each other such that both the front haptic and the rear haptic can be slid onto and/or to the optical portion of the lens by a single actuation.

In a first embodiment of a coupled movement of the haptic sliders, the cartridge comprises a link member mounted for being moved, preferably rotated. The link member is connected to each of the front haptic slider and the rear haptic slider through a respective rotary joint.

The coupled movement is in particular induced when the cartridge is slidingly fitted on the cannula of the injector. The link member is caused to completely abut on a rear portion of the cannula. This causes a rotation of the link member, which in turn results in an opposite movement of the two sliders.

In a second embodiment of a coupled movement, the cartridge comprises an axially displaceable carriage in which the receiving region for the lens is provided. The carriage is displaced towards the rear haptic slider by an axial displacement of the front haptic slider. First, the front haptic slider displaces the front haptic towards the optical portion of the lens. The haptic slider comes to rest against the carriage and displaces it towards the rear haptic slider. The lens is thereby displaced towards the rear haptic slider. As a result, the rear lens haptic also approaches the optical portion of the lens. The rear haptic slider itself is not moved thereby.

In a further embodiment, the cartridge is distinguished by having a respective ramp arranged on a portion of the cartridge, preferably on the inner surface of the two sidewalls. Preferably, a ramp rising from the front end toward the rear end of the cartridge is provided for the front haptic. Preferably, a ramp rising from the rear end toward the front end of the cartridge is provided for the rear haptic. The ramps do not need to extend completely through the cartridge. In a further embodiment, a respective ramp is provided on each of the inner surfaces of the cartridge having an initial upslope starting from the front end of the cartridge and then a downslope towards the rear end of the cartridge. Preferably, the receiving region for the at least one lens is provided by a respective recess in the ramp which is preferably disposed approximately centrally. In the initial, non-displaced state, the haptic tip of the front lens haptic and the haptic tip of the rear lens haptic are supported on the ramp next to the receiving region. This allows the lens as a whole to be stored in a substantially stress-free state. Alternatively, biasing of the lens, for example by pre-folding the lens, is possible as well.

In a further embodiment, at least two heads are provided in each receiving region for the lens, which are adapted to support a peripheral area of the optical portion of the lens. This allows to reduce the contact area between the cartridge and the lens.

Also within the scope of the invention is an injector system for or including the cartridge as described above. This is an injector system for implanting a lens into an eye, comprising:
  an injector body having a front end and a rear end;
  a cannula arranged at the front end of the injector body, which provides a transport channel for a lens to be implanted, wherein a lens can be fed into the transport channel via a preferably lateral inlet opening;
  an embodiment of the cartridge described above and below, comprising a receiving region for at least one lens, wherein the cartridge is arranged such that a lens can be fed into the transport channel via the preferably lateral inlet opening;

a folding body which is insertable into the cartridge and into the inlet opening, for pushing the lens into the transport channel in such a manner that the lens is foldable around the folding body, at least portions thereof; and a slider which is arranged within the injector body so as to be displaceable, preferably axially, and which can be pushed through the front end of the injector body and into the transport channel in such a way that the lens can be ejected from the transport channel.

In one embodiment, the cartridge is connectable with the cannula and preferably can be slidingly fitted or plugged onto the cannula of the injector in a manner so that the cannula is arranged in the interior of the cartridge or on the cartridge, at least a portion thereof, for loading the injector system with a lens.

In a preferred embodiment of the invention, the cartridge is provided as a separate module. The cartridge may already be factory-mounted on the injector, or may be fastened only by the user.

The cartridge preferably has an outlet area or outlet opening which is arranged so as to be aligned with the inlet opening of the transport channel, so that by means of the folding body the lens can be pushed from the cartridge through the outlet area or outlet opening into the transport channel. In this variant, the cannula can be directly inserted into the cartridge which is preferably disposed in a separate container, and may be latched therewith or therein, for example, so that a functional unit is established. Preferably, the cartridge and/or the lens are stored under sterile conditions within the container.

The cartridge and/or injector system according to the invention is particularly suitable for all soft, foldable intraocular lenses. Such lenses are for example made of acrylic, silicone and/or hydrogel material. The cartridge of the invention is easily adaptable to different types of lenses, in particular in terms of the geometry/design and/or material thereof.

The specific dimensions and/or shapes of the individual modules and/or the features of the cartridge and/or of the injector system depend on the design of an intraocular lens to be implanted, inter alia. The cartridge and/or the injector of the invention can be used as a preloaded disposable or single-use injector.

BRIEF DESCRIPTION OF THE DRAWINGS

The present invention will now be described in more detail by way of the following exemplary embodiments. For this purpose, reference is made to the accompanying drawings. The same reference numerals in the individual drawings refer to the same parts.

FIGS. 1.a. and 1.b show the injector according to the invention in its assembled state (with the folding body not yet introduced), in a perspective view (FIG. 1.a) and in a side view (FIG. 1.b).

FIGS. 2.a to 2.c are perspective views illustrating the front end portion of the injector with the cannula and with the cartridge fitted on the cannula with the folding body not yet inserted (FIG. 2.a), with inserted folding body (FIG. 2.b), and once again without folding body (FIG. 2.c).

FIGS. 3.a to 3.c are perspective views illustrating the cartridge according to a first embodiment in different states: with the laterally mounted haptic sliders (FIG. 3.a), without haptic sliders (FIG. 3.b), and without a lens (FIG. 3.c).

FIGS. 4.a to 4.c illustrate a haptic slider, in a side view of its inner surface (FIG. 4.a), in a side view of its outer surface (FIG. 4.b), and in a perspective view of the underside of its head portion (FIG. 4.c).

FIGS. 5.a to 5.c are perspective views showing the operation steps in the preparation of the injector for inserting the lens into the eye: the cartridge in its initial state (FIG. 5.a), with the rear haptic applied (FIG. 5.b), and with the front haptic applied (FIG. 5.c).

FIGS. 6.a to 6.f show a second embodiment of a cartridge comprising two haptic sliders mounted laterally on the cartridge walls and extending through the cartridge wall: in two perspective views laterally from above (FIGS. 6.a and 6.b), in a plan view (FIG. 6.c), in a plan view with transparent walls (FIG. 6.d), and in a side view with transparent walls (FIGS. 6.e and 6.f).

FIGS. 7.a to 7.e are perspective views showing a third embodiment of a cartridge comprising two haptic sliders that have their movement coupled to each other: the cartridge without haptic slider (FIG. 7.a), with inserted haptic sliders in the initial state thereof (FIG. 7.b), and in the final state thereof with the haptics applied on the lens (FIG. 7.c), and with the cannula illustrated (FIGS. 7.d and 7.e).

FIGS. 8.a and 8.b are perspective views showing a fourth embodiment of a cartridge comprising two haptic sliders which also have their movement coupled: the cartridge in the initial state (FIG. 8.a), and in the final state with the haptics applied on the lens (FIG. 8.b).

DETAILED DESCRIPTION OF THE INVENTION

The cartridge according to the invention will now be described by way of an exemplary modular injector system 100. For this purpose, FIG. 1 shows an injector 100 in its assembled state. The modules of the injector 100 include a housing 10, a slider 20, a cannula 30, and the cartridge 40 of the invention.

The cannula 30 is arranged at the front end 10a of housing 10. Cannula 30 and housing 10 are joint together, for example by a snap-fit. Cannula 30 has a transport channel 31 for the lens 90, for delivering the lens 90 from the injector 100 and inserting the lens 90 into an eye. Cartridge 40 is placed on, preferably plugged onto cannula 30. Preferably, cannula 30 and cartridge 40 are snap-fitted to each other.

Folding flap 50 carrying folding rib 51 is positioned in its not yet folded-down state. Therefore, the lens 90 is not yet located in the transport channel 31 of cannula 30. The injector 100 is still locked, so to speak.

By pivoting down the folding flap (for this see FIG. 2.b), the lens 90 is transferred into the transport channel 31 of the cannula 30. The injector 100 will then be unlocked, so to speak. The injector 100 is ready for use. The slider 20 is inserted from the rear end 10b of housing 10. It is arranged so as to be axially displaceable within housing 10. Slider 20 is disposed in housing 10 so as to exit from the front end 10a of the housing 10 such that it can enter the transport channel 31 of cannula 30. Slider 20 and transport channel 31 are matched to each other in shape and/or size so that the slider 20 is also axially displaceable in the transport channel 31. By moving or pushing the slider 20 towards the front end 100a of the injector 100, the lens 90 which is located in the transport channel 31 of cannula 30 is ejected from the injector 100.

The front end 30*a* of cannula 30 or of transport channel 31 defines the outlet opening for the lens 90. The slider 20 or the injector 100 can be actuated, for example, by applying the index finger and the middle finger on grips 11 of housing 10 and engaging the thumb in the handle 21 of slider 20.

For further details about loading or equipping, locking, unlocking, and/or applying the injector 100 or ejecting the lens, reference is made to the description of FIGS. 5.*a* through 5.*c* and to WO 2012/155887 A1. In the example shown, the cartridge 40 has already been pre-assembled on the injector 100, in particular at the factory.

FIGS. 2.*a* and 2.*b* show a detailed view of the front end portion of the injector 100. Shown are the cannula 30 and the cartridge 40 fitted to the cannula 30. FIG. 2.*a* directly shows the injector 100 of FIGS. 1.*a* and 1.*b*. The cartridge 40 is attached, in particular plugged, to the cannula 30, preferably by a snap-fit. Cartridge 40 includes the lens 90 disposed therein. The folding body 50 for introducing the lens 90 into the transport channel 31 of the cannula 30 is attached to the injector body 10. Folding body 50 consists of two parts here, a base 51-1, and a folding rip 51-2 displaceable within the base 51-2. For further details refer to the description of FIG. 5.*c* below.

FIGS. 2.*b* and 2.*c* (as well as FIGS. 3.*a* to 4.*c*) show a variant slightly modified in comparison to the cartridge 40 illustrated in FIG. 2.*a*. Haptic sliders 60 and 60' each have a projection 61 on the top, which is intended to serve in particular as a grip surface for a finger for moving. FIG. 2.*b* shows the state in which the folding body 50 has been pivoted down and the lens 90 has been transferred into the transport channel 31 of cannula 30 and thereby has been folded substantially into a U-shaped profile around folding body 50. It should be noted here that the haptic sliders 60 and 60' are shown in a non-displaced state in FIG. 2.*b*. FIG. 2.*c* shows again the view of FIG. 2.*b*, but without folding body 50. The cannula 30 is mounted on the injector body 10 by means of a latching connection 33.

FIGS. 3.*a* to 3.*d* now illustrate the cartridge 40 as such. In order to better illustrate and explain the details of cartridge 40, particular components have sometimes been omitted in the individual figures. The two haptics 91 and 92 of the lens 90 have not yet been urged onto the lens 90 or the optical portion of the lens 90. Thus, the two haptic sliders 60 and 60' are still in their initial state.

First, FIG. 3.*a*. illustrates the complete cartridge 40 with the two haptic sliders 60 and 60' assembled. Explanations on the structure and function will be given for only one haptic slider 60, but are applicable to the other haptic slider 60' as well (see also FIGS. 4.*a* to 4.*c*). Haptic slider 60 is disposed on the sidewall 43 of cartridge 40. It is mounted for being displaceable on the sidewall 43, preferably axially. For this purpose, a rail 46 is formed on top of the sidewall 43, on which the haptic slider 60 can slide.

Haptic slider 60 has a recess 62 on its inner portion 64. This recess 62 defines a receiving region for the haptic tip of the rear haptic 91 in this case. When the cartridge 40 is being stored, the haptic tip is reliably captured there. However, the recess 62 also defines a driver for the haptic tip when the haptic slider 60 is displaced (for this see the description of FIGS. 5.*a* to 5.*c*).

FIG. 3.*b* now illustrates the cartridge 40 without assembled haptic sliders 60 and 60'. FIG. 3.*c* shows the same view, but with the lens 90 removed. Cartridge 40 includes a type of ramp 45 formed on the inner surface of sidewall 43, which is preferably curved, at least in sections thereof. Ramp 45 initially rises from the front end 100*a* of the injector 100 and then falls off again approximately from a middle section. Approximately in the middle of the ramp 45, the receiving region 44 for the lens 90 is provided. Receiving region 44 is provided in the form of a recess in the ramp 45 here. The shape or contour of receiving region 44 is substantially adapted to the contour of the lens 90. Preferably, the contour of the receiving region is curved, at least in sections thereof. Lens 90 is supported on or in the receiving region 44 for the lens 90, in particular the haptic root of the front haptic 91' and a peripheral area of the optical portion of the lens 90, in this case. By contrast, the haptic tip of the rear haptic 91 is not located in the receiving region 44, here. The haptic tip is supported next to the receiving region 44 on the down-sloping area of ramp 45. The same also applies to the other side of the lens 90 and the ramp 45 to the right, which is only partially shown here. As a result, the two haptics 91 and 91' and the optical portion of the lens 90 can essentially lie on the same level and can therefore be stored in a preferably stress-free state. Furthermore, since the two haptics 91 and 91' are supported on the ramp 45, they are displaceable. The receiving region 44 furthermore includes two heads 44*a*, which are distributed along the longitudinal axis, here. This allows the optical portion of the lens 90 to be supported in particular on a small area.

However, the two haptic sliders 60 and 60' do not only perform the function of shifting the haptics 91, 91' or sliding the haptics 91 and 91' onto the lens 90. They also perform the function of a retainer for the lens 90 in the cartridge 40 or in the receiving region 44 for the lens 90. The haptic slider 60 covers, with its inner portion 64, the receiving region 44 for the lens 90, both in its initial state and in its displaced final state (for this see FIGS. 3.*a* and 5.*a* through 5.*c*).

FIGS. 4.*a* to 4.*c* now show the haptic slider 60 and 60' as such. First, FIG. 4.*a* shows a view of the inner portion 64 of haptic slider 60. It is curved here, in particular on its underside, so that it can slide accordingly on the likewise curved ramp 45. On the underside of the inner portion 64, the recess 62 for receiving and driving the haptic tip of haptics 91, 91' is provided. The head portion 65 of haptic slider 60 features a projection 61 which provides a grip surface for a finger when displacing the haptic slider 60, for example.

FIG. 4.*b* shows a view of the outer portion 63 of haptic slider 60. In order to better illustrate the inner structure of the haptic slider 60, FIG. 4.*c* shows the haptic slider 60 in a view turned upside down on the "head", showing the outer portion 63, the inner portion 64, and the connecting head portion 65. The haptic slider 60 is attached to the cartridge 40 substantially through the outer portion 63. For this purpose, the outer portion 63 has a projection 66 on its inner surface. Projection 66 engages behind the rail 46 formed on top of the cartridge sidewall 43. The rail 46 is thereby mounted or captured between the underside of head portion 65 and the projection 66 of the outer portion 63 so as to allow for axial displacement. However, the inner surface of the inner portion 64 of haptic slider 60 is flat. It is guided on the inner surface of cartridge sidewall 43.

FIGS. 5.*a* to 5.*c* illustrate the operation steps in the preparation of the injector 100 for inserting the lens 90 into the eye.

FIG. 5.*a* shows the injector 100 with the preferably pre-assembled cartridge 40, for example after removal from the packaging. Lens haptics 91 and 91' and haptic sliders 60 and 60' are still in their initial state. Starting, by way of example, with the haptic slider 60 shown on the right here, and associated with the rear haptic 91. For this purpose, the haptic slider 60 is shifted towards the front end 100*a* of the injector 100 (in the direction of the arrow). Thereby, the haptic slider entrains the haptic 91 or haptic tip thereof until the latter comes to rest and/or abut on a peripheral area of the lens 90, preferably partially or completely. The haptic 91 may contact the optical portion of the lens. But it may also be positioned above the lens 90 spaced therefrom. The haptic tip may also be urged out of the recess 62 in the haptic slider 60, so that it only contacts the inner surface of the haptic slider 60. In this final position, the haptic slider 60 may latch with the cartridge 40, for example. FIG. 5.*b* shows the haptic slider 60 shifted forward and the haptic tip of the rear haptic also slid forward and applied on the optical portion.

Basically the same procedure is now performed for the front haptic 90'. For this purpose, the front haptic slider 60' shown on the left here, is shifted towards the rear end 100*b* of the injector 100 (direction of arrow in FIG. 5.*b*). Thereby, it entrains the haptic tip until the latter preferably comes to rest on the peripheral area of the lens 90. The haptic tip may also be urged out of the recess 62 in the haptic slider 60' such that it only contacts the inner surface of the haptic slider 60'. In this final position, the haptic slider 60' may again latch with the cartridge 40. FIG. 5.*c* shows the haptic slider 60' shifted rearward and the haptic tip of the front haptic 91' applied on the optical portion.

The lens 90 is now configured so that it can be folded. The lens 90 is folded by pivoting down the folding body 50 and introducing it into the cartridge 40 (for this see FIG. 2.*b*, for example), and is thereby also introduced into the transport channel 31 of the cannula 30. The slider 20 then conveys the lens 90 towards and out of the front end 100*a* of the injector 100 (not illustrated in the figures). During shifting and ejecting of the lens 90, the latter is rolled up. Since they have been displaced, the haptics 91 and 91' are in particular arranged such that they are positioned in defined manner during the folding process and after folding so that they can be wrapped into the lens 90 during the process of ejecting the lens 90. So, the haptics 91 and 91' cannot hinder insertion of the lens 90 into the eye, for example. Once the lens 90 has been introduced into the eye, it unfolds and the haptics 90 and 91' assume their positions.

The operation of the injector 100 is described once again below, but is not illustrated in the figures (for this see in particular WO 2012/155887 A1). In a next step, the injector 100 is unlocked. For this purpose, the lens 90 is moved or transferred from its initial position in the cartridge 40 to its transport position in the cannula 30 or in the transport channel 31. The transport position mentioned indicates the position from which the lens 90 can be ejected from the injector 100 and inserted into an eye using the slider 20. For this purpose, folding flap 50 is folded or pivoted towards the top of cartridge 40. Folding rib 51 located at the underside of folding flap 50 passes between the two haptic sliders 60 and 60' and engages in cartridge 40. Folding flap 51 engages on the upper surface of lens 90 and urges the lens out of its initial position in the cartridge 40 and into the transport channel 31 of cannula 30 while folding the lens 90 into a U-shaped profile. To ensure reliably folding of the lens 90 and to prevent possible slipping or jamming of lens 90, a pair of retaining ledges 52 is preferably provided at folding rib 51. Folding body 51 consists two parts here. It comprises a base 51-1 in which the actual folding element 51-2 is mounted. The retaining ledges 52 are provided by the base 51-1. The folding element 51-2 is arranged in the base 51-1 so as to be displaceable towards the upper surface of folding body 51. Without the provided retaining ledges 52, the lens 90 could slide laterally upwards and jam.

In a next step, the lens 90 is ejected from the injector 100 and introduced into an eye. By means of the slider 20, the lens 90 is pushed out of the injector 100. During continuous advancement which causes the lens 90 to be rolled up, the two haptics 91 and 91' are wrapped into the lens 90. Thus, they have a defined position when the lens 90 is ejected.

FIGS. 6.*a* to 6.*f* show a second embodiment of a cartridge 40 comprising two haptic sliders 160 and 160' that are mounted laterally, to the cartridge walls 43. Slider 160 is associated with the rear haptic 91, and slider 160' is associated with the front haptic 91'. The underlying functional principle here essentially corresponds to that of the first embodiment described above. In the present case, the two haptic sliders 160 and 160' each extend through a respective opening 47 in the sidewall 43 of the cartridge 40 (for this see in particular FIG. 6.*d*).

For this purpose, the two haptic sliders 160 and 160' each have an outer portion 161 and 161', respectively, and an inner portion 162 and 162', respectively. The respective outer portion 161 or 161' serves as a grip surface for the fingers of the user for moving the haptic slider 160 or 160'. The respective inner portion 162 or 162' extends through the opening 47 in the cartridge wall 43. It provides the driver for the respective haptic tip.

The two openings 47 are each inclined upwards toward the center of the cartridge 40, here. They form a ramp for the two haptic sliders 160 and 160'. This allows the two haptics 91 and 91' to be intentionally guided onto the upper surface of the lens 90. FIGS. 6.*a* to 6.*e* show each of the two haptic sliders 160 and 160' in their initial state, with the haptics 91 and 91' not yet displaced.

FIGS. 7.*a* to 7.*e* show a third embodiment of a cartridge 40 comprising two haptic sliders 260 and 260'. In this embodiment, the movement of the two haptic sliders 260 and 260' is coupled. First, FIG. 7.*a* shows the cartridge 40 still without the two haptic sliders 260 and 260'. Lens 90 is located in its receiving region 44 within the cartridge 40. A recess 48 is provided in the rear end of cartridge 40. Recess 48 provides the pivot point for a link member 262.

FIG. 7.*b* shows the link member 262 and the two haptic sliders 260 and 260' in their initial state. The two end portions of haptic sliders 260 and 260' are at a different axial position. Link member 262 is coupled with the two haptic sliders 260 and 260' through a respective rotary joint 261. Link member 262 thus provides a connection between the two haptic sliders 260 and 260' via a double joint. The link member 262 and the two haptic sliders 260 and 260' may be formed in one piece, for example. In such an implementation, the two joints 261 may be provided by a respective living hinge, for example. In particular a pin (not shown in the figures) can be provided on an underside of link member 262, which engages in the recess 48 in cartridge 40 to provide the pivot point.

The two haptic sliders 260 and 260' may be mounted in the cartridge 40 in or on a type of rail 49, for example, in particular so as to be axially movable. The rail 49 is provided here by a respective groove (see FIG. 7.*a*). Rails 49 provide for a guided movement of the two haptic sliders 260 and 260'.

The two haptic sliders 260 and 260' engage on the haptic roots in the present example. Although a larger force is required for moving the haptics 91 and 91' in this way, however, this shortens the path over which the two sliders 260 and 260' have to travel.

Through the double joint 261, the link member 262 provides for a coupled movement of the two haptic slider 260 and 260'. FIG. 7.*c* shows the final state. The two haptics 91 and 91' are illustrated both in their initial state and in their final state in which they are applied on the lens 90. The transfer to the final state or the movement of the haptic sliders 260 and 260' is caused by slidingly mounting the cartridge 40 onto the cannula 30, here. This is again shown in FIGS. 7.*d* and 7.*e*.

FIGS. 7.*d* and 7.*e* illustrate the underlying principle of this embodiment. For this purpose, the cannula 30 of the injector 100 is furthermore shown here. For loading the injector 100, the cartridge 40 equipped with the lens 90 is slidingly fitted onto the cannula 30. The advancement direction is indicated by the arrow (FIG. 7.*d*). The rear portion of link member 262 comes into abutment on an end portion of cannula 30. When the cartridge 40 is further advanced onto the cannula 40, the link member 262 causes the two haptic sliders 260 and 260' to move relative to the sidewalls 43 of the cartridge, by virtue of the double-jointed connection 261. On the one hand, slider 260 is displaced toward the front end of the cannula 30 thereby sliding the rear haptic 91 to or onto the lens 90. On the other hand, slider 260' is simultaneously displaced toward the rear end of the cannula 30, thereby sliding the front haptic 91' to or onto the lens 90.

In FIG. 7.*e*, the cartridge 40 has been slidingly fitted completely on cannula 30. In this state, the link member 262 is completely abutting on the end portion of cannula 30. The two haptic sliders 260 and 260' are in their final position, here. The two haptics 91 and 91' are applied on the lens 90, although the shifted final position of the two haptics is not illustrated in FIG. 7.*e*.

Finally, FIGS. 8.*a* and 8.*b* show a fourth embodiment of a cartridge 40 comprising two haptic sliders 360 and 360'. The cartridge 40 has already been slidingly fitted onto the cannula 30 of the injector 100. FIG. 8.*a* shows the two haptic sliders 360 and 360' in their initial state, FIG. 8.*b* in their final state.

The two haptic sliders 360 and 360' are movably mounted on the cartridge 40. They are placed on the sidewalls 43 of the cartridge 40. The rear haptic slider 360 does not move itself relative to the cannula 30. The receiving region 44 for the lens 90 is located within a carriage 361. The carriage 361 can be moved axially relative to the cannula 30.

First, the front haptic slider 360' is shifted towards the rear end of the injector 100. It comes to abut on the front haptic 91' and moves it towards the lens 90. Furthermore, the front haptic slider 360' then abuts on the carriage 361. By further shifting the front haptic slider 360', the carriage 361 with the lens 90 accommodated therein is therefore also shifted towards the rear haptic slider 360. The rear haptic 91 is thereby caused to abut on the rear haptic slider 360. The rear haptic 91 will thereby be displaced forward towards the lens 90.

FIG. 8.*b* shows the final state of cartridge 40, in which the front haptic slider 360' and the carriage 361 are abutting on the rear haptic slider 360. The two haptics 91 and 91' contact the lens 90 or are applied on the lens 90.

It will be apparent to a person skilled in the art that the above described embodiments are meant as an example only. The invention is not limited to these embodiments, rather it may be modified in many ways without departing from the spirit of the invention.

Features of particular embodiments can be combined with each other as well as with the features mentioned in the general part of the description.

LIST OF REFERENCE NUMERALS

10 Injector body, or injector housing, or housing, or handset
11 Grips on injector body
20 Slider, or plunger, or lens slider
21 Handle, or slider handle
30 Cannula, or tube for insertion into the eye, or body for discharging the lens
31 Transport channel or advancement channel
33 Lug on cannula or latching lug
40 Cartridge, or container for storing the lens
43 Sidewall of cartridge
44 Receiving region for a lens
44*a* Heads or elevations in receiving region
45 Ramp or guidance area for a lens haptic
46 Rail or guide rail for haptic slider
47 Opening in sidewall of cartridge
48 Recess in cartridge
49 Rail or groove in cartridge
50 Folding flap, or folding plate support, or flap
51 Folding body, or folding plate, or folding rib
51-1 Base of folding body
52-2 Folding element of folding body
52 Retaining ledge on folding plate
52*d* Underside of retaining ledge
60 Haptic slider (for rear haptic)
60' Haptic slider (for front haptic)
61 Projection on haptic slider
62 Receiving region and driver for haptic tip
63 Outer portion of haptic slider
64 Inner portion of haptic slider
65 Head portion of haptic slider
66 Projection or latching projection
90 Lens, or intraocular lens, or optical portion of lens
91 (Rear) haptic of lens
91' (Front) haptic of lens
100 Injector, or injector system, or applicator
100*a* Front end of injector
100*b* Rear end of injector
160 Haptic slider (for rear haptic)
160' Haptic slider (for front haptic)
161 Outer portion or section of (rear) haptic slider
161' Outer portion or section of (front) haptic slider
162 Inner portion or section of (rear) haptic slider and driver for haptic tip
162' Inner portion or section of (front) haptic slider and driver for haptic tip
260 Haptic slider (for rear haptic)
260' Haptic slider (for front haptic)
261 Rotary joint or hinge
262 Link member (between haptic sliders)
360 Haptic slider (for rear haptic)
360' Haptic slider (for front haptic)
361 Carriage within cartridge

The invention claimed is:

1. An injector system for implanting a lens into an eye, comprising:
   an injector body having a front end and a rear end;
   a cannula arranged at the front end of the injector body, which provides a transport channel for the lens to be implanted;
   a cartridge comprising a receiving region for the lens and at least one movable haptic slider for displacing a lens haptic within the cartridge, wherein the cartridge is arranged such that the lens can be fed into the transport channel;
   a folding body insertable into the cartridge and receiving region of the lens, for pushing the lens into the transport channel in such a manner that the lens is foldable around the folding body; and a slider arranged within the injector body so as to be displaceable, and which can be pushed through the front end of the injector body and into the transport channel in such a way that the lens can be ejected from the transport channel, wherein the haptic slider is mounted to the cartridge so as to be movable.

2. The injector system as claimed in claim 1, wherein the cartridge is connected with the cannula so that the cannula is arranged either in an interior of the cartridge, at least a portion thereof, and/or on the cartridge.

3. The injector system as claimed in claim 1, wherein the haptic slider is adapted such that a lens is captured within the receiving region in both, an initial state and a displaced state of the haptic slider.

4. The injector system as claimed in claim 1, wherein the haptic slider provides a driver for a haptic tip of the lens haptic.

5. The injector system as claimed in claim 1, further comprising a projection for moving the haptic slider, where the projection is formed on a head portion or on an outer portion of the haptic slider.

6. The injector system as claimed in claim 1, wherein the haptic slider is arranged on a sidewall or a bottom of the cartridge so as to be displaceable substantially axially.

7. The injector system as claimed in claim 1, wherein the haptic slider is mounted to a sidewall of the cartridge and extends into the cartridge through an opening in the sidewall of the cartridge.

8. The injector system as claimed in claim 1, wherein the haptic slider comprises a rear haptic slider associated with a rear haptic, and a front haptic slider associated with a front haptic.

9. The injector system as claimed in claim 1, wherein the haptic slider comprises a rear haptic slider and a front haptic slider are displaceable in opposite directions.

10. The injector system as claimed in claim 1, wherein the haptic slider comprises a rear haptic slider for sliding the rear haptic, the rear haptic slider is displaceable towards a front end of the injector, or wherein the haptic slider comprises a front haptic slider for sliding the front haptic, the front haptic slider is displaceable towards a rear end of the injector.

11. The injector system as claimed in claim 1, wherein the haptic slider comprises a front haptic slider and a rear haptic slider, and wherein the injector system comprises a link member mounted for being moved and connected to each of the front haptic slider and the rear haptic slider through a respective rotary joint.

12. The injector system as claimed in claim 1, wherein the haptic slider comprises a front haptic slider and a rear haptic slider, and wherein the injector system comprises an axially displaceable carriage wherein the receiving region for the lens is provided, wherein said carriage is displaceable towards the rear haptic slider by an axial displacement of the front haptic slider.

13. The injector system as claimed in claim 1, wherein a respective ramp is provided on a portion of the cartridge.

14. The injector system as claimed in claim 1, wherein in an initial state, each of a haptic tip of a front lens haptic and a haptic tip of a rear lens haptic are supported on a ramp next to the receiving region for the lens.

15. The injector system as claimed in claim 1, wherein a lens is stored within the receiving region of the cartridge in a substantially stress-free state or in a pre-folded state.

16. The injector system as claimed in claim 1, wherein the at least one movable haptic slider is configured to slide the lens haptic onto or to an optical portion of the lens.

17. An injector system for implanting a lens into an eye, comprising:
    an injector body having a front end and a rear end;
    a cannula arranged at the front end of the injector body, which provides a transport channel for the lens to be implanted;
    a cartridge comprising a receiving region for the lens, wherein the cartridge is arranged such that the lens can be fed into the transport channel;
    a folding body insertable into the cartridge and into the receiving region of the lens, for pushing the lens into the transport channel in such a manner that the lens is foldable around the folding body; and
    a slider arranged within the injector body so as to be displaceable, and which can be pushed through the front end of the injector body and into the transport channel in such a way that the lens can be ejected from the transport channel, wherein
    the cartridge comprises a rear haptic slider and a front haptic slider within the cartridge for displacing a lens haptic within the cartridge, and
    the rear haptic slider and the front haptic slider are displaceable in opposite directions.

18. An injector system for implanting a lens into an eye, comprising:
    an injector body having a front end and a rear end;
    a cannula arranged at the front end of the injector body, which provides a transport channel for the lens to be implanted;
    a cartridge comprising a receiving region for the lens, wherein the cartridge is arranged such that the lens can be fed into the transport channel;
    a folding body insertable into the cartridge and into the receiving region of the lens, for pushing the lens into the transport channel in such a manner that the lens is foldable around the folding body; and
    a slider arranged within the injector body so as to be displaceable, and which can be pushed through the front end of the injector body and into the transport channel in such a way that the lens can be ejected from the transport channel, wherein
    the cartridge comprises a front haptic slider and a rear haptic slider within the cartridge for displacing a lens haptic within the cartridge, and
    the rear haptic slider and the front haptic slider are coupled such that both the front haptic and the rear haptic can be slid onto or to an optical portion of the lens by a single actuation.

19. An injector system for implanting a lens into an eye, comprising:
    an injector body having a front end and a rear end;
    a cannula arranged at the front end of the injector body, which provides a transport channel for the lens to be implanted;
    a cartridge comprising a receiving region for the lens and at least one movable haptic slider for displacing a lens haptic within the cartridge, wherein the cartridge is arranged such that the lens can be fed into the transport channel;
    a folding body insertable into the cartridge and into the receiving region of the lens, for pushing the lens into the transport channel in such a manner that the lens is foldable around the folding body; and a slider arranged within the injector body so as to be displaceable, and which can be pushed through the front end of the injector body and into the transport channel in such a way that the lens can be ejected from the transport channel, wherein a respective ramp is provided having an initial upslope from a front end of the cartridge and then a downslope towards a rear end of the cartridge.

20. An injector system for implanting a lens into an eye, comprising:

an injector body having a front end and a rear end;

a cannula arranged at the front end of the injector body, which provides a transport channel for the lens to be implanted;

a cartridge comprising a receiving region for the lens and at least one movable haptic slider for displacing a lens haptic within the cartridge, wherein the cartridge is arranged such that the lens can be fed into the transport channel;

a folding body insertable into the cartridge and into the receiving region of the lens, for pushing the lens into the transport channel in such a manner that the lens is foldable around the folding body; and a slider arranged within the injector body so as to be displaceable, and which can be pushed through the front end of the injector body and into the transport channel in such a way that the lens can be ejected from the transport channel, wherein the receiving region for the lens is provided by a respective recess in a ramp.

21. An injector system for implanting a lens into an eye, comprising:

an injector body having a front end and a rear end;

a cannula arranged at the front end of the injector body, which provides a transport channel for the lens to be implanted; a cartridge comprising a receiving region for the lens and at least one movable haptic slider for displacing a lens haptic within the cartridge, wherein the cartridge is arranged such that the lens can be fed into the transport channel;

a folding body insertable into the cartridge and into the receiving region of the lens, for pushing the lens into the transport channel in such a manner that the lens is foldable around the folding body; and a slider arranged within the injector body so as to be displaceable, and which can be pushed through the front end of the injector body and into the transport channel in such a way that the lens can be ejected from the transport channel, wherein at least two heads are provided thein each receiving region for the lens adapted to support an optical portion of the lens.

* * * * *